(12) United States Patent
Srinivasan et al.

(10) Patent No.: US 12,390,813 B2
(45) Date of Patent: Aug. 19, 2025

(54) MICROFLUIDICS SYSTEM, DEVICE, AND METHODS FOR PERFORMING RAPID POLYMERASE CHAIN REACTION (PCR) PROTOCOLS

(71) Applicant: Baebies, Inc., Durham, NC (US)

(72) Inventors: Vijay Srinivasan, Durham, NC (US); Vamsee Pamula, Durham, NC (US); Daniel Wu, Durham, NC (US); Rainer Ng, Durham, NC (US); Richard Gell, Durham, NC (US); Jennifer Elderbroom, Durham, NC (US); Abigail Jackson, Durham, NC (US)

(73) Assignee: Baebies, Inc., Durham, NC (US)

( * ) Notice: Subject to any disclaimer, the term of this patent is extended or adjusted under 35 U.S.C. 154(b) by 0 days.

(21) Appl. No.: 18/827,295

(22) Filed: Sep. 6, 2024

(65) Prior Publication Data

US 2024/0424498 A1 Dec. 26, 2024

Related U.S. Application Data

(63) Continuation of application No. PCT/US2023/083048, filed on Dec. 8, 2023.

(60) Provisional application No. 63/386,619, filed on Dec. 8, 2022.

(51) Int. Cl.
*C12Q 1/68* (2018.01)
*B01L 3/00* (2006.01)
*B01L 7/00* (2006.01)

(52) U.S. Cl.
CPC ......... *B01L 7/525* (2013.01); *B01L 3/502792* (2013.01); *B01L 2200/0647* (2013.01); *B01L 2200/16* (2013.01); *B01L 2300/0645* (2013.01); *B01L 2300/161* (2013.01); *B01L 2300/1805* (2013.01); *B01L 2400/0427* (2013.01)

(58) Field of Classification Search
None
See application file for complete search history.

(56) References Cited

U.S. PATENT DOCUMENTS

| | | | |
|---|---|---|---|
| 9,452,433 B2* | 9/2016 | Shenderov | B01L 3/502792 |
| 10,378,010 B2* | 8/2019 | Zhang | C12Q 1/6874 |
| 2012/0204577 A1* | 8/2012 | Ludwig | G06F 1/20 |
| | | | 62/3.3 |
| 2013/0059366 A1* | 3/2013 | Pollack | B01L 3/502715 |
| | | | 435/287.2 |
| 2014/0194305 A1* | 7/2014 | Kayyem | B01L 3/502784 |
| | | | 506/18 |

(Continued)

*Primary Examiner* — Aaron A Priest
(74) *Attorney, Agent, or Firm* — E. Eric Mills; Nicholas P. Stadnyk; Maynard Nexsen PC

(57) ABSTRACT

The subject matter relates generally to performing polymerase chain reaction (PCR) in microfluidics devices and more particularly to a microfluidics system, device, and methods for performing rapid polymerase chain reaction (PCR) protocols. In some embodiments, the presently disclosed subject matter provides a microfluidics system including a microfluidics instrument housing a microfluidics cartridge (or device) along with any supporting components. Further, the microfluidics cartridge may be, for example, any fluidics device or cartridge, microfluidics device or cartridge, DMF device or cartridge, droplet actuator, flow cell device or cartridge, and the like.

18 Claims, 28 Drawing Sheets

(56) References Cited

U.S. PATENT DOCUMENTS

2015/0259754 A1\* 9/2015 Kaler ................ B01L 3/502792
                                                    506/9
2018/0001286 A1\* 1/2018 Wu ........................ B01F 35/92

\* cited by examiner

MICROFLUIDICS SYSTEM, DEVICE, AND METHODS FOR PERFORMING RAPID POLYMERASE CHAIN REACTION (PCR) PROTOCOLS

CROSS REFERENCE TO RELATED APPLICATIONS

This application is a continuation of International Patent Application No. PCT/US2023/083048 filed Dec. 8, 2023, which claims the benefit of U.S. Provisional Application No. 63/386,619, filed Dec. 8, 2022, which are incorporated by reference herein in their entireties.

TECHNICAL FIELD

The subject matter relates generally to performing polymerase chain reaction (PCR) in microfluidics devices and more particularly to a microfluidics system, device, and methods for performing rapid PCR protocols.

BACKGROUND

Microfluidics systems, devices, and/or cartridges are used to process biological materials. In these processes, thermocycling of the biological materials being processed may occur. For example, in PCR protocols, biological materials may be cycled between an annealing temperature, an extension temperature, and a denaturation temperature. The annealing temperature may be, for example, from about 55° C. to about 60° C. The extension temperature may be, for example, from about 68° C. to about 72° C. The denaturation temperature may be, for example, from about 94° C. to about 98° C.

This thermocycling may occur at a certain rate or frequency. The total processing time may be fully or in part dependent on the thermocycling rate or frequency. Currently, however, the thermocycling rate or frequency in microfluidics processes may be limited. This, in turn, may be a limiting factor with respect to reducing the overall processing time when using microfluidics, which may be a particular detriment in point-of-care (POC) applications.

BRIEF DESCRIPTION OF DRAWINGS

Figure 1:
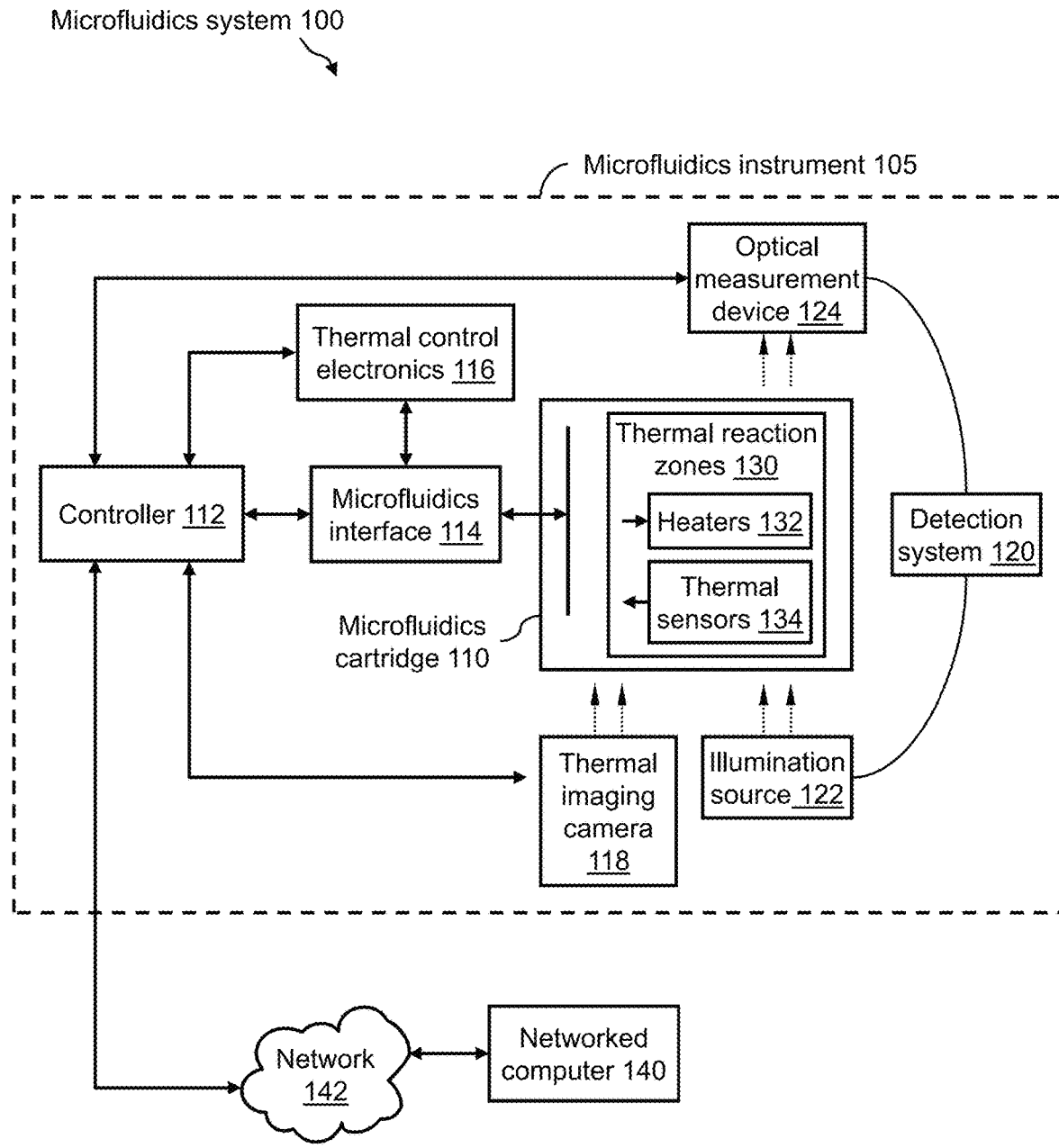
Figure 2A:
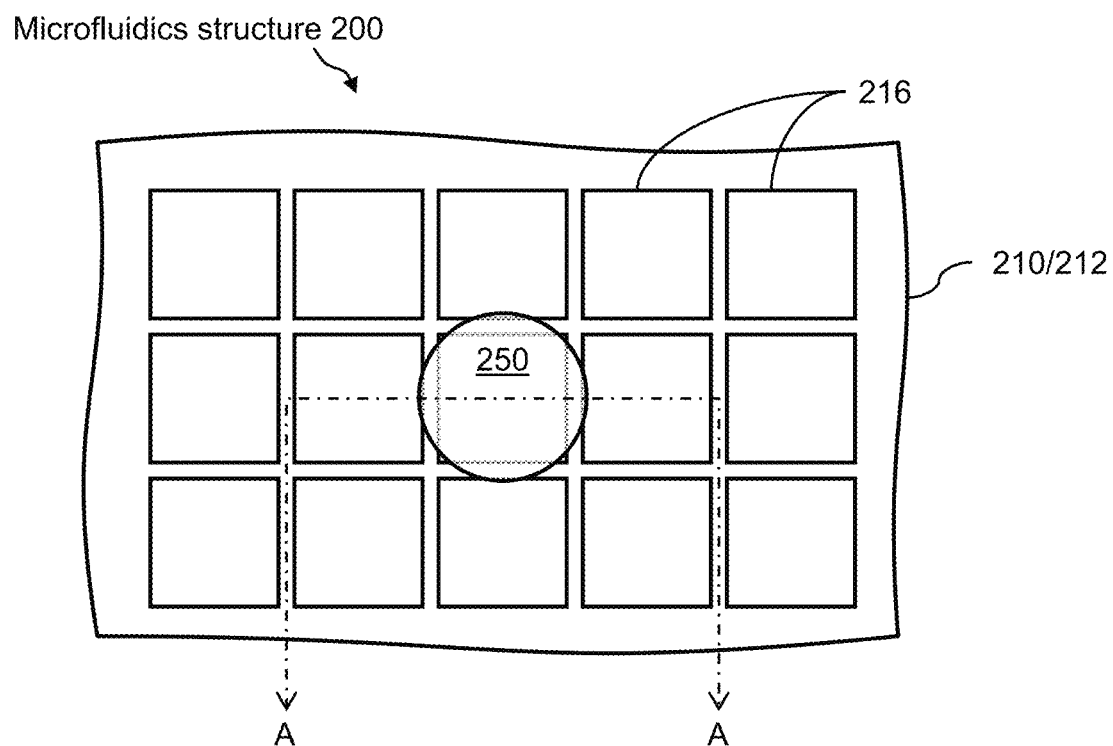
Figure 2B:
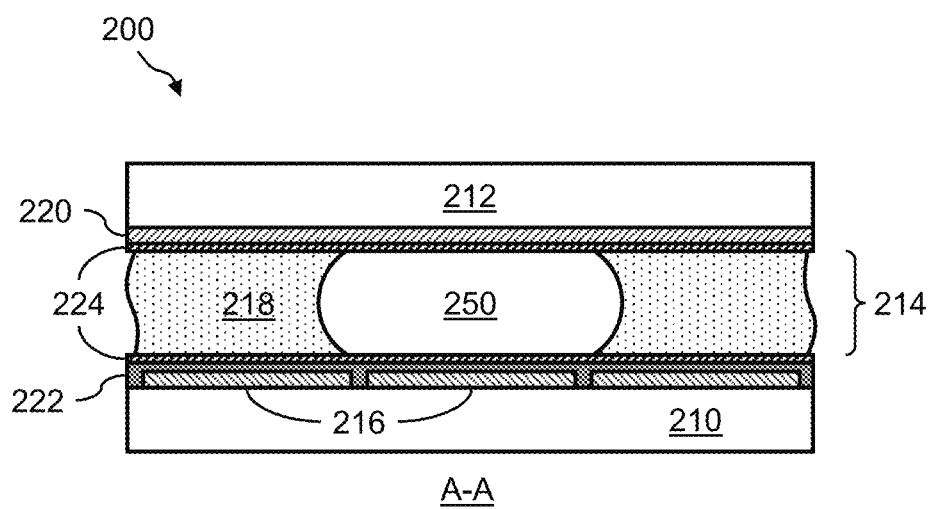
Figure 3:
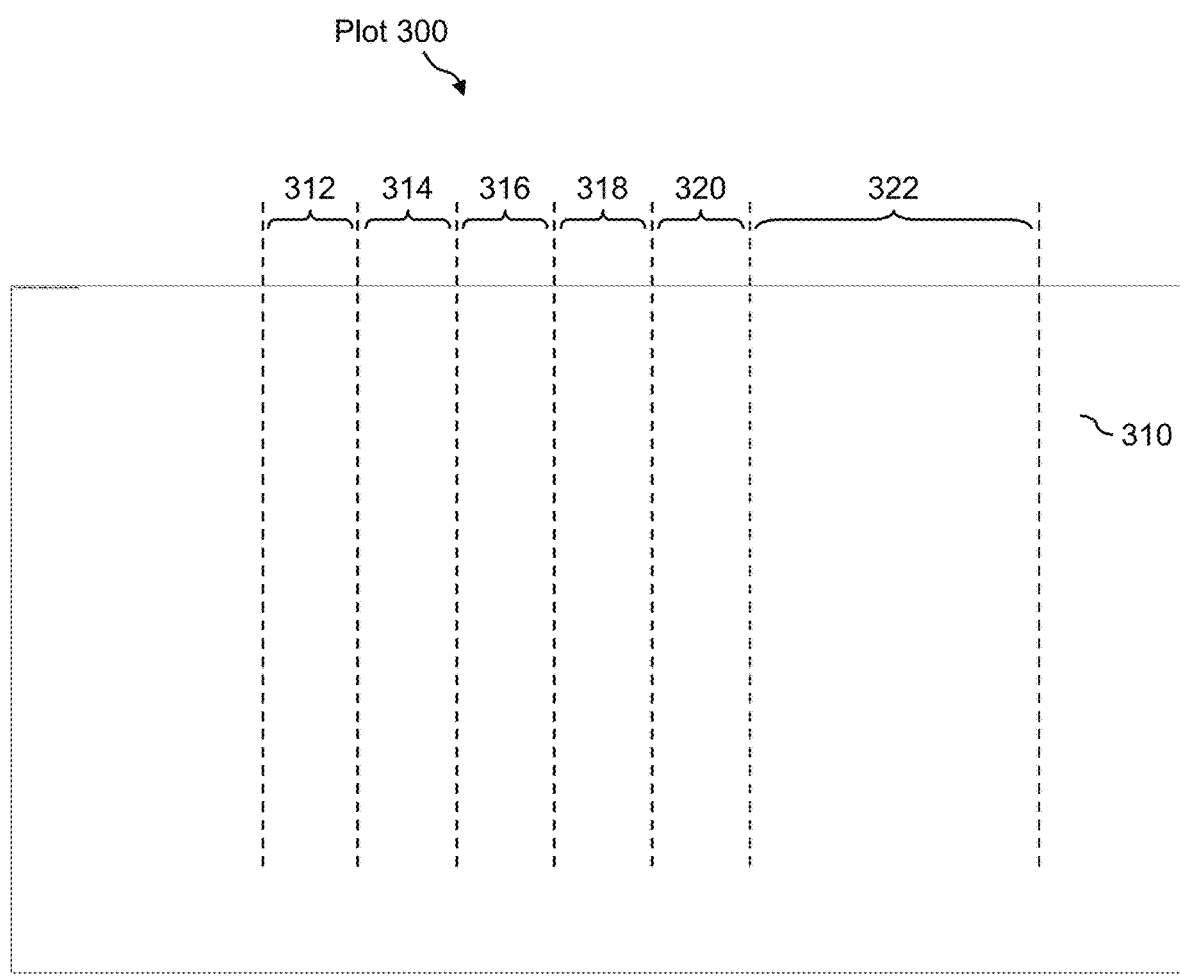
Figure 4A:
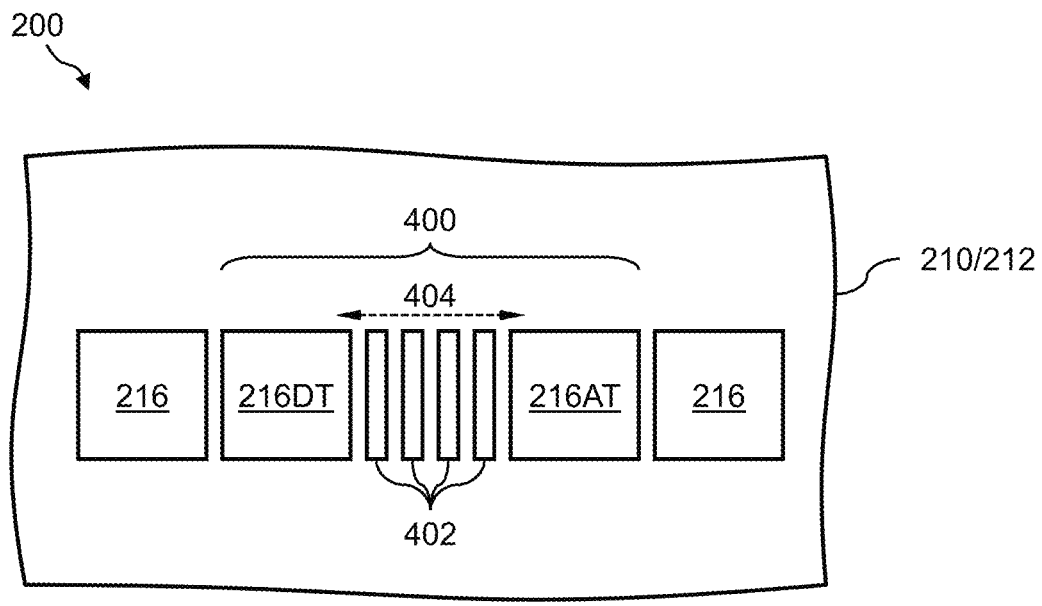
Figure 4B:
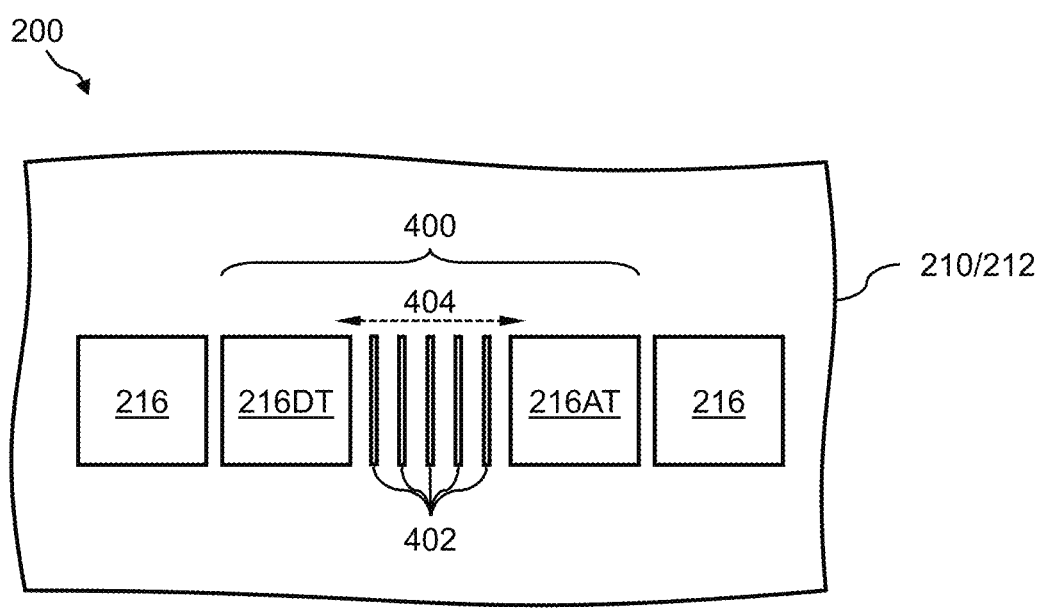
Figure 5A:
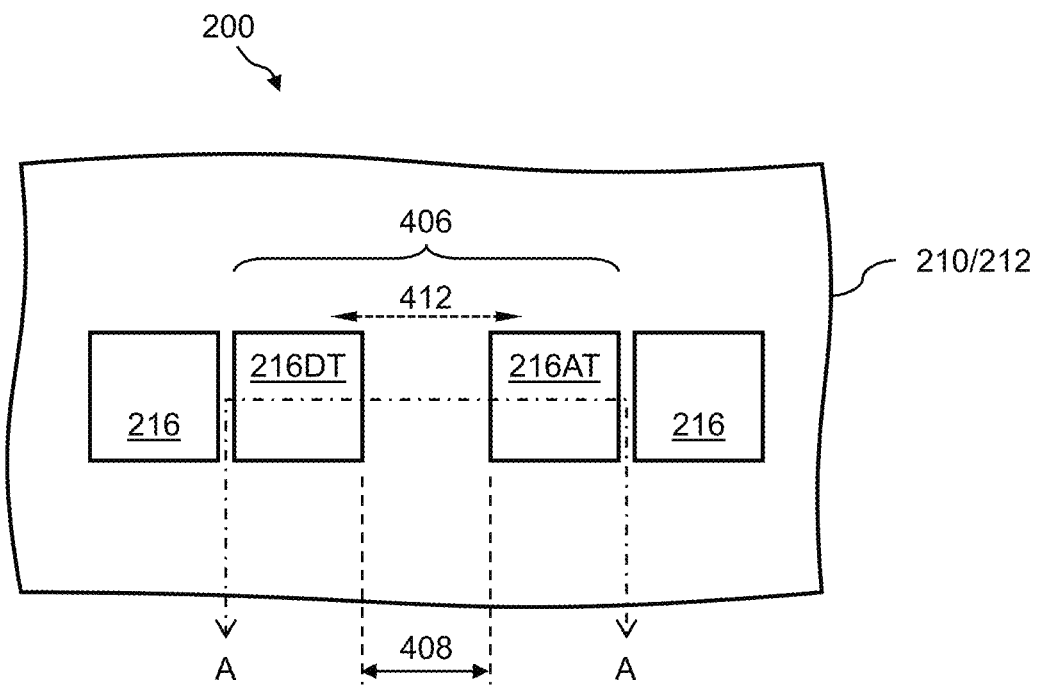
Figure 5B:
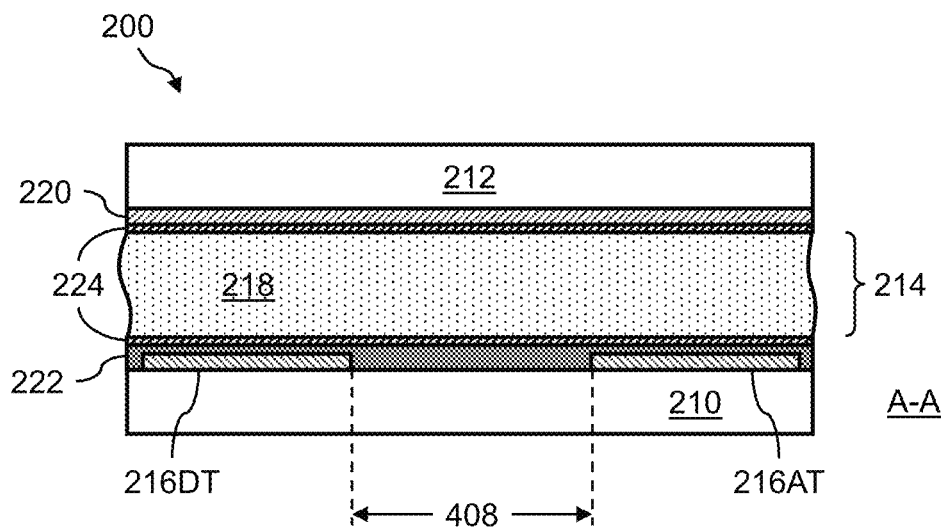
Figure 6A:
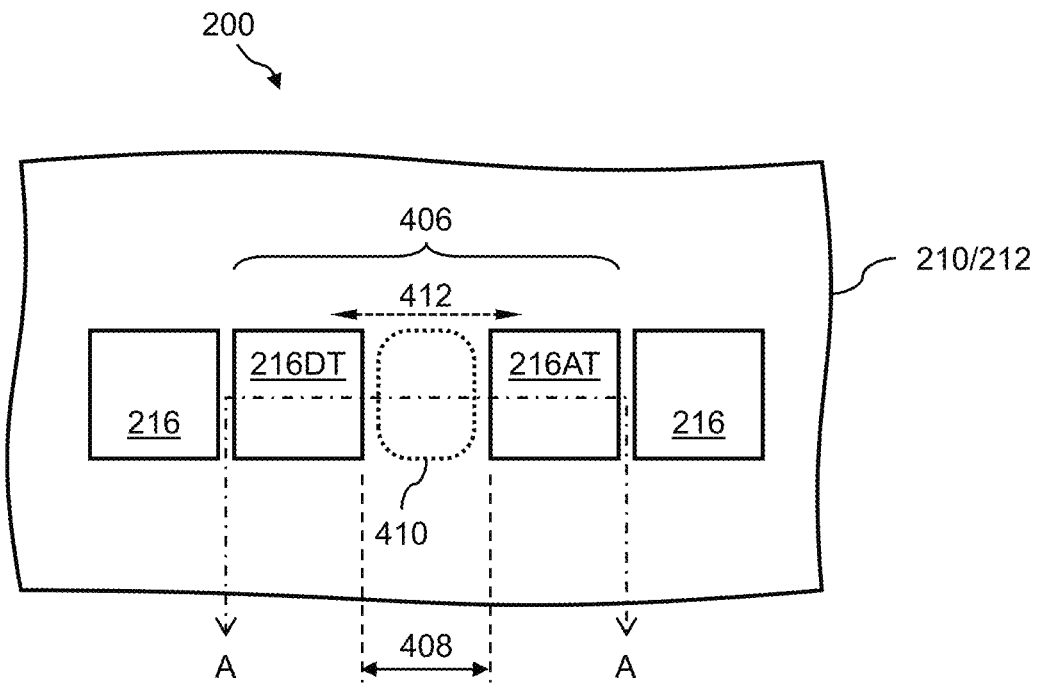
Figure 6B:
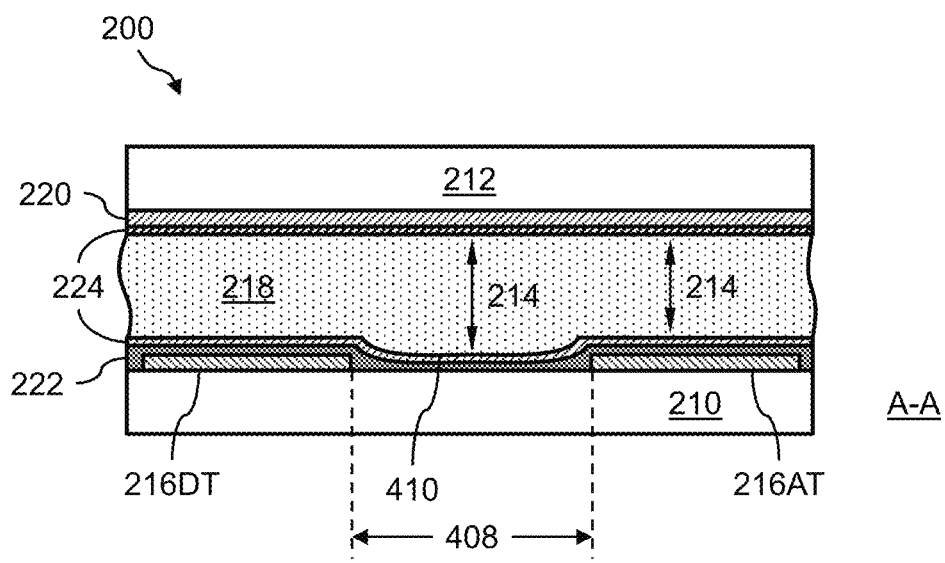
Figure 7A:
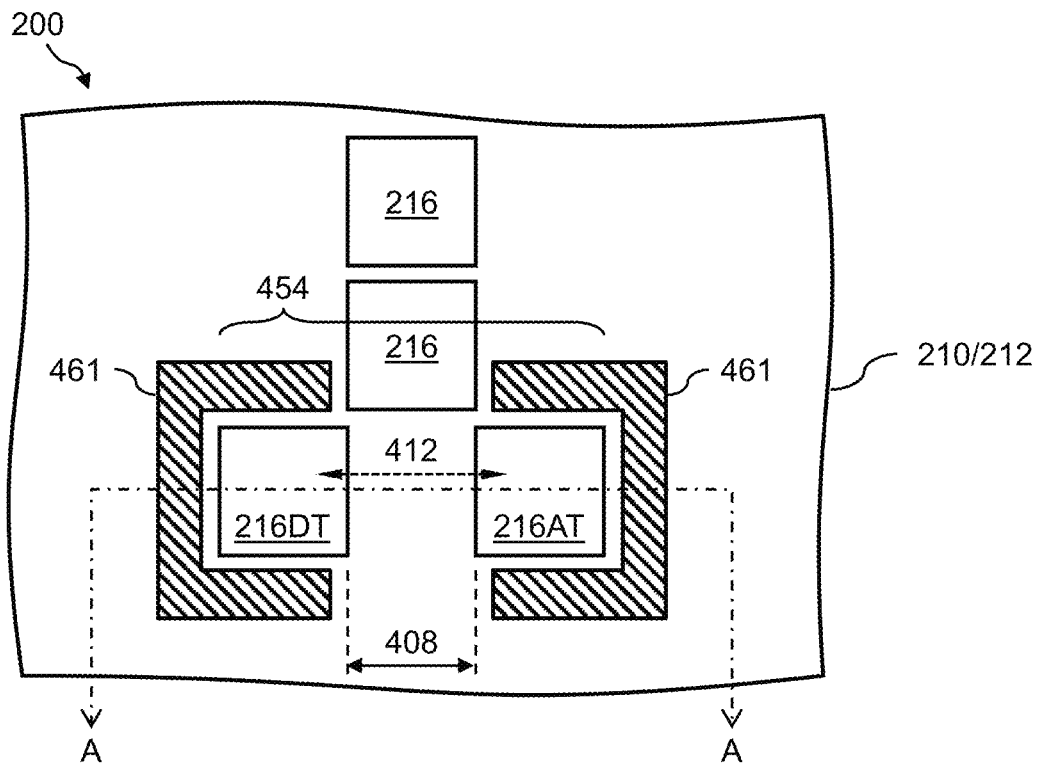
Figure 7B:
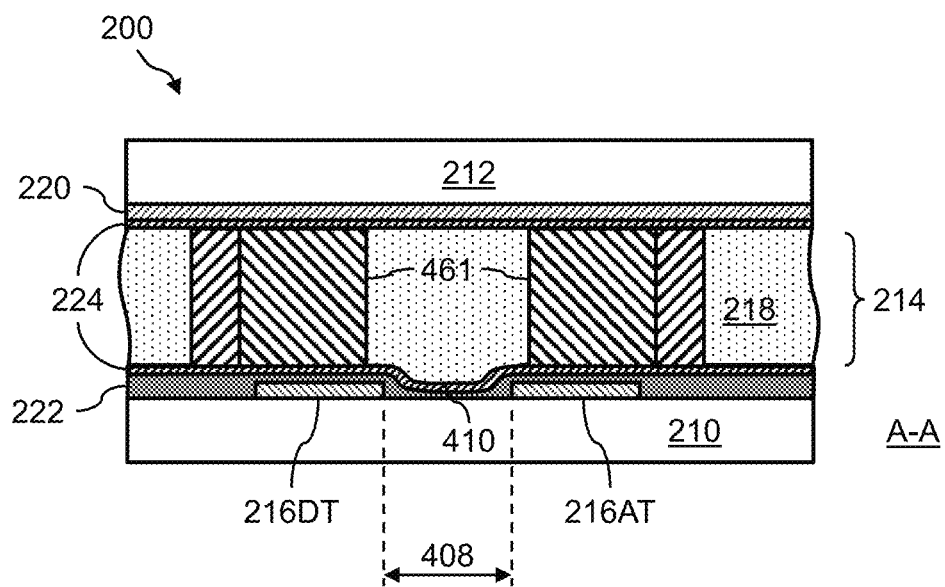
Figure 8A:
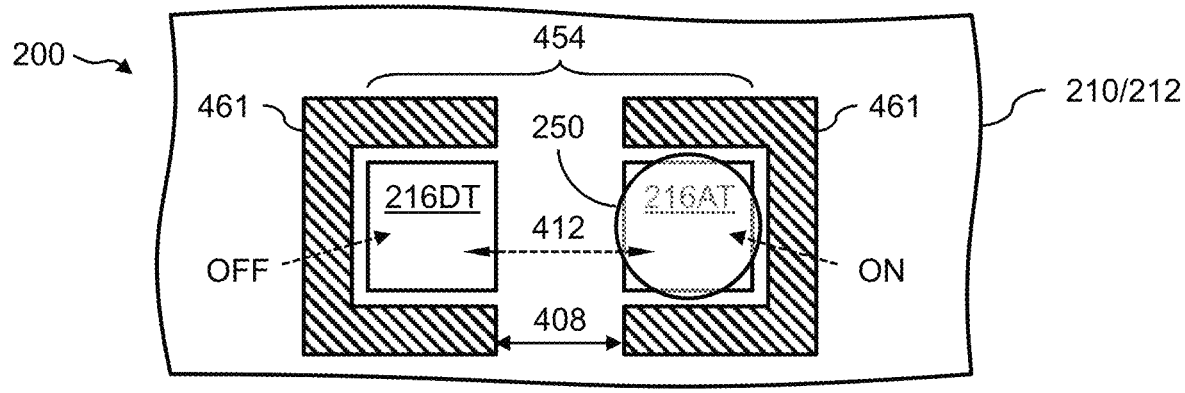
Figure 8B:
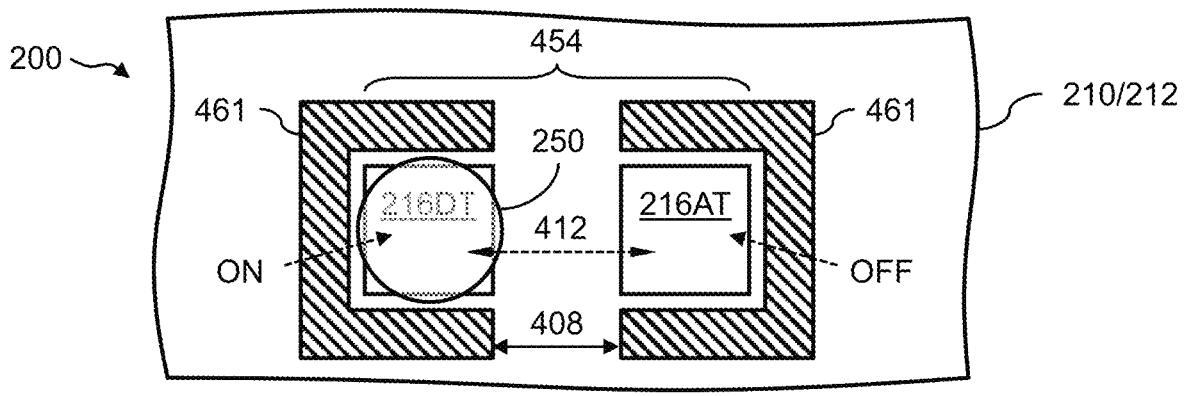
Figure 8C:
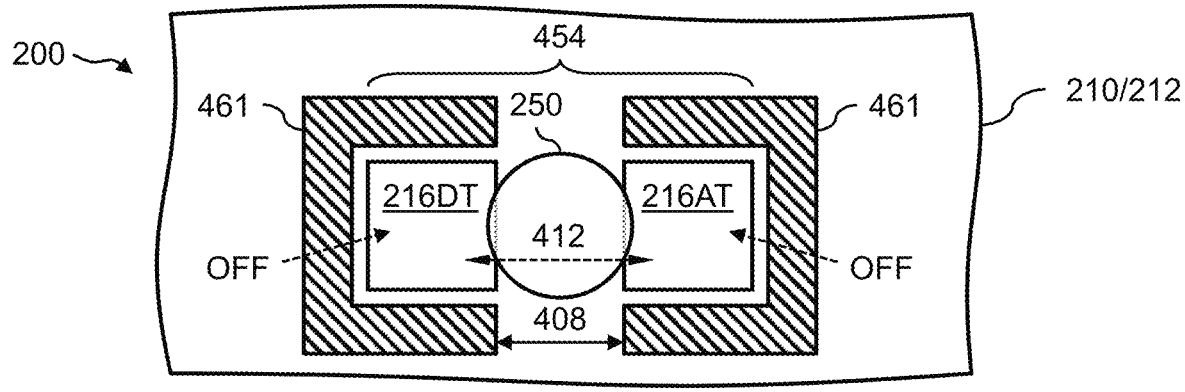
Figure 9A:
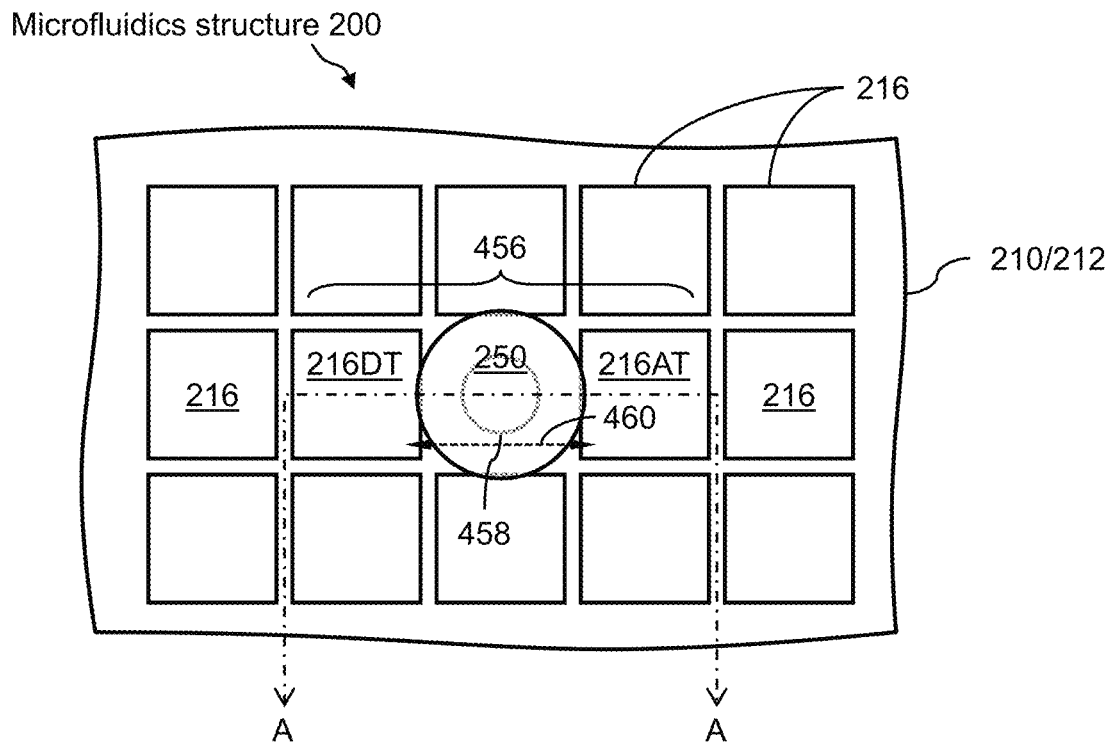
Figure 9B:
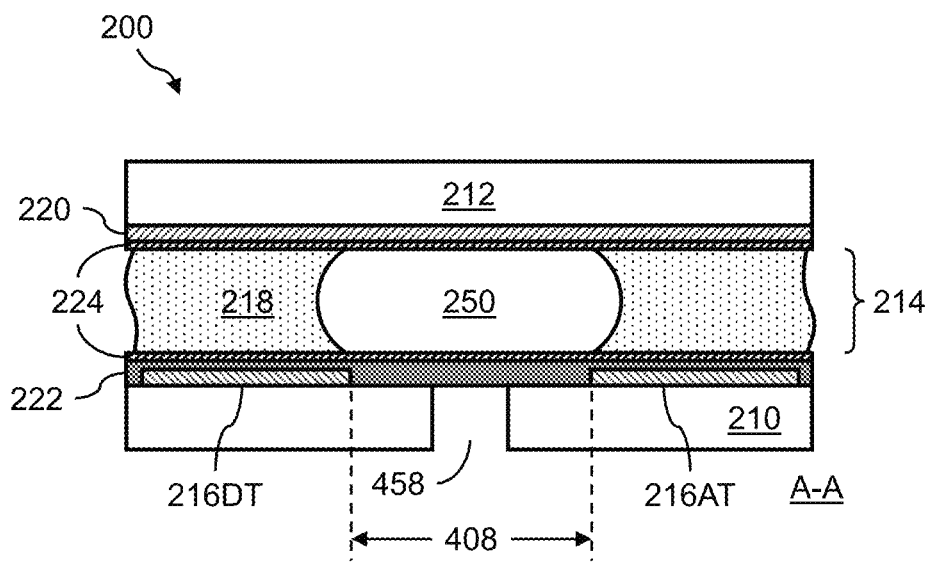
Figure 10:
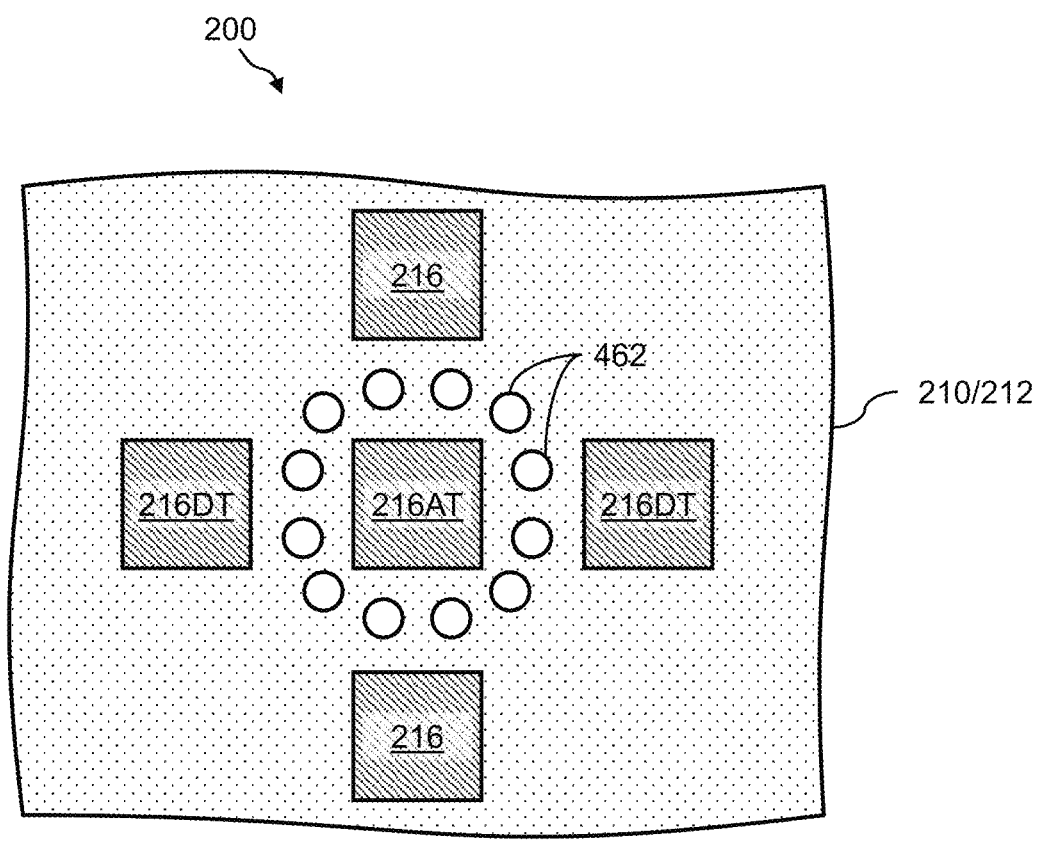
Figure 11A:
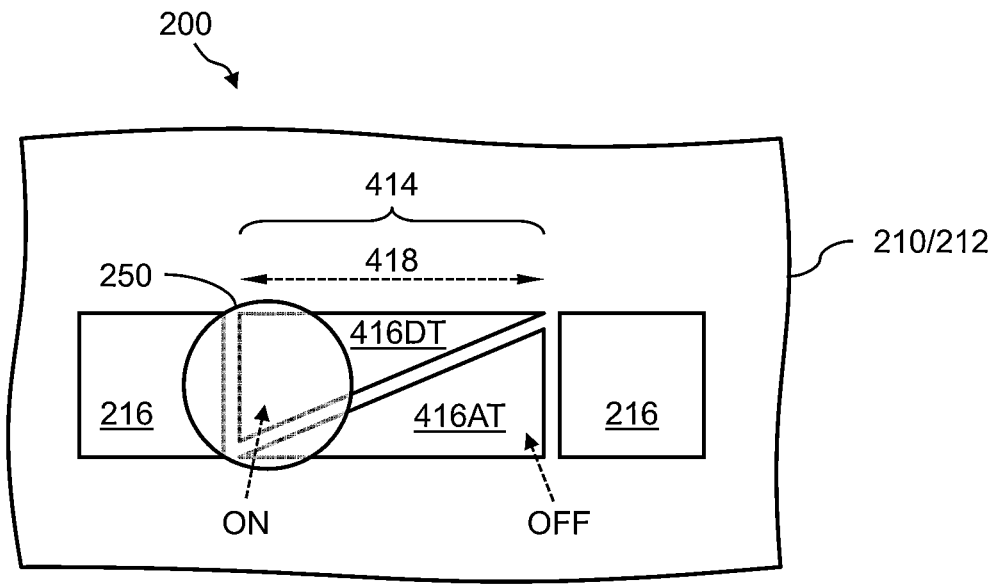
Figure 11B:
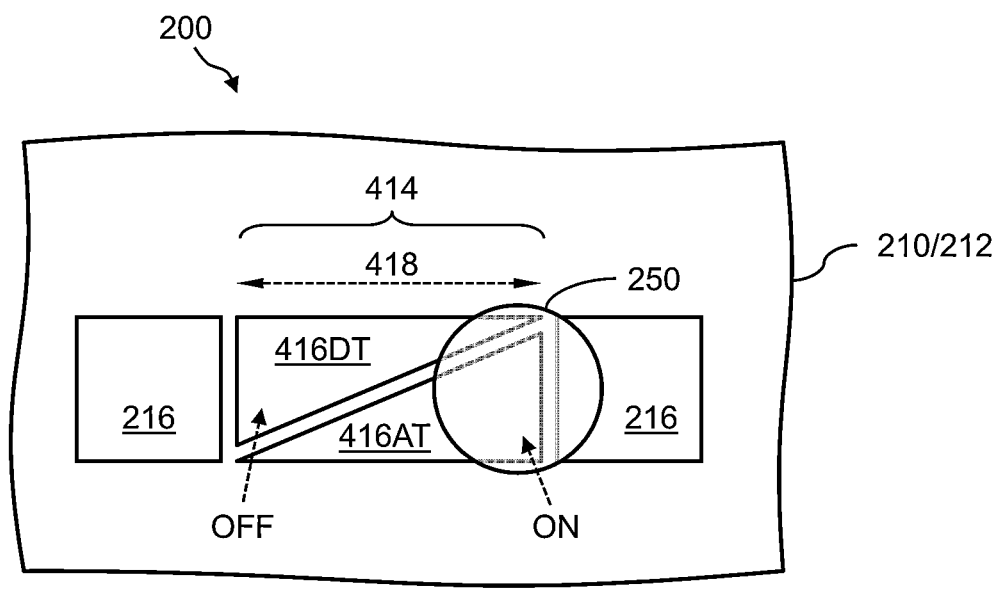
Figure 12A:
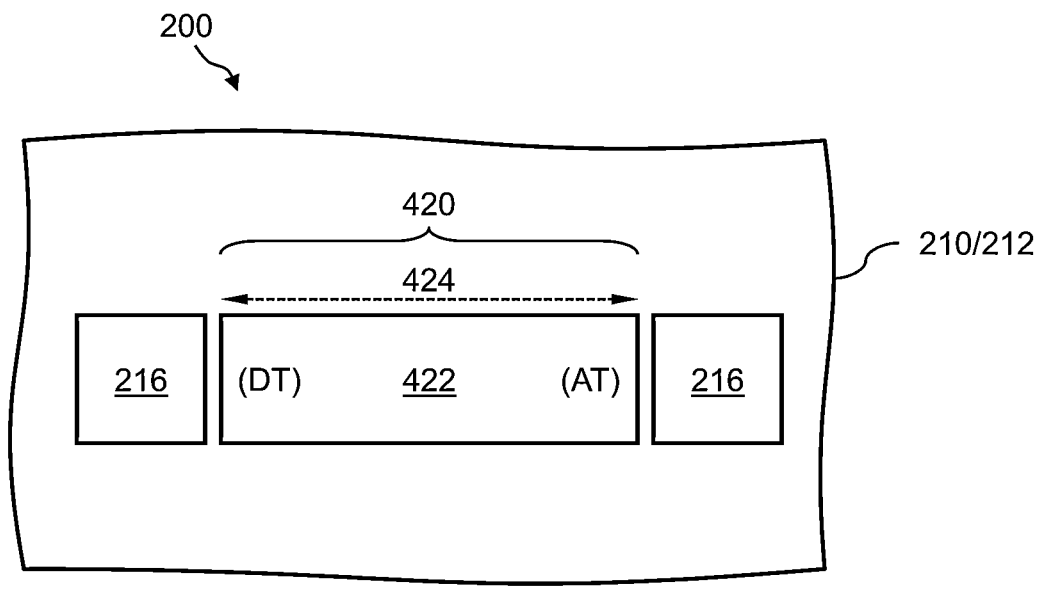
Figure 12B:
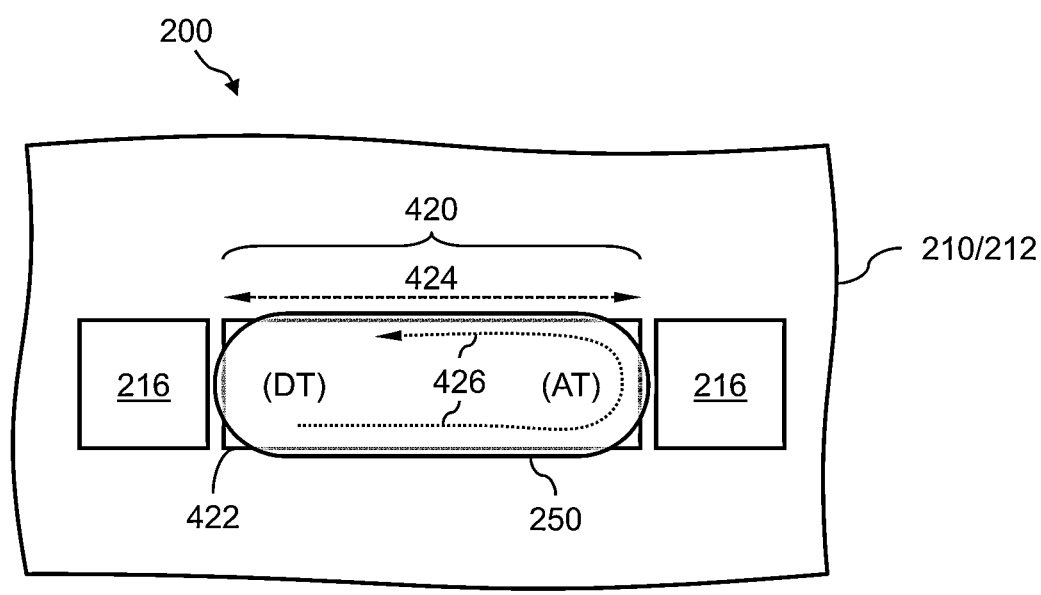
Figure 13A:
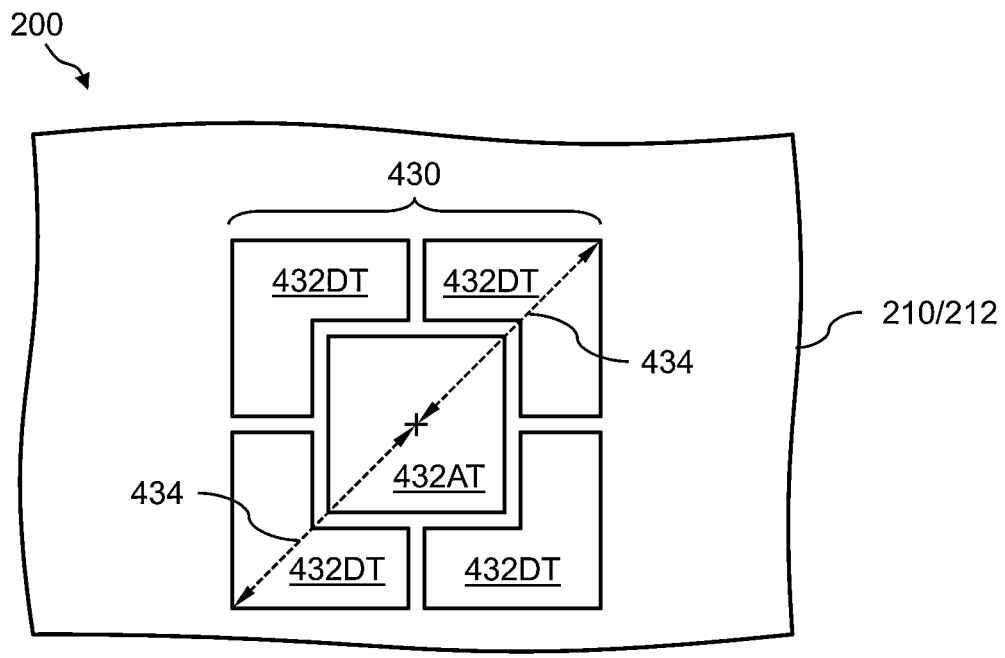
Figure 13B:
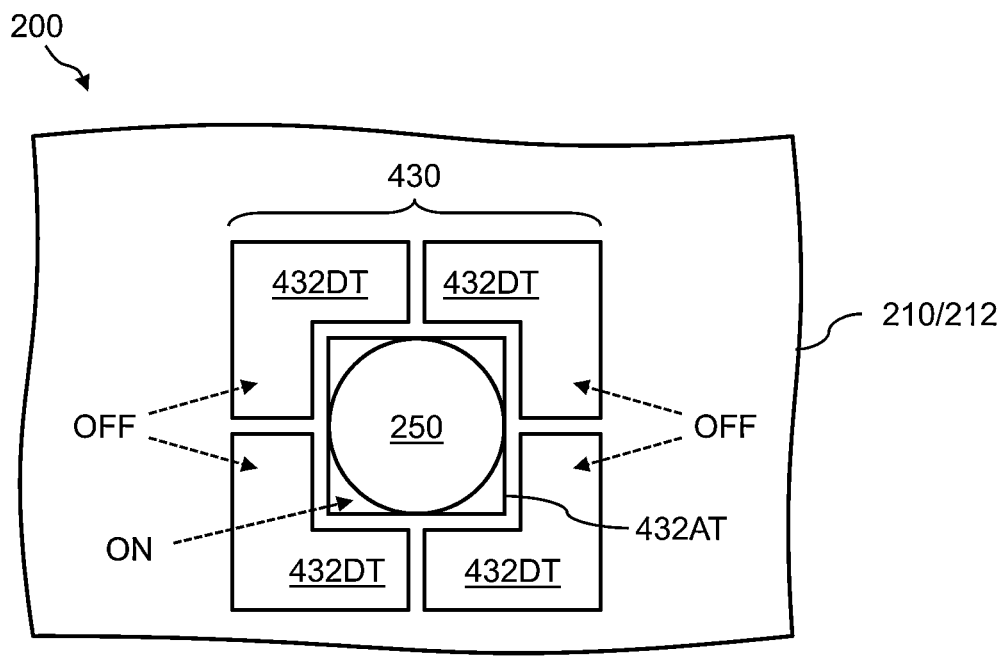
Figure 13C:
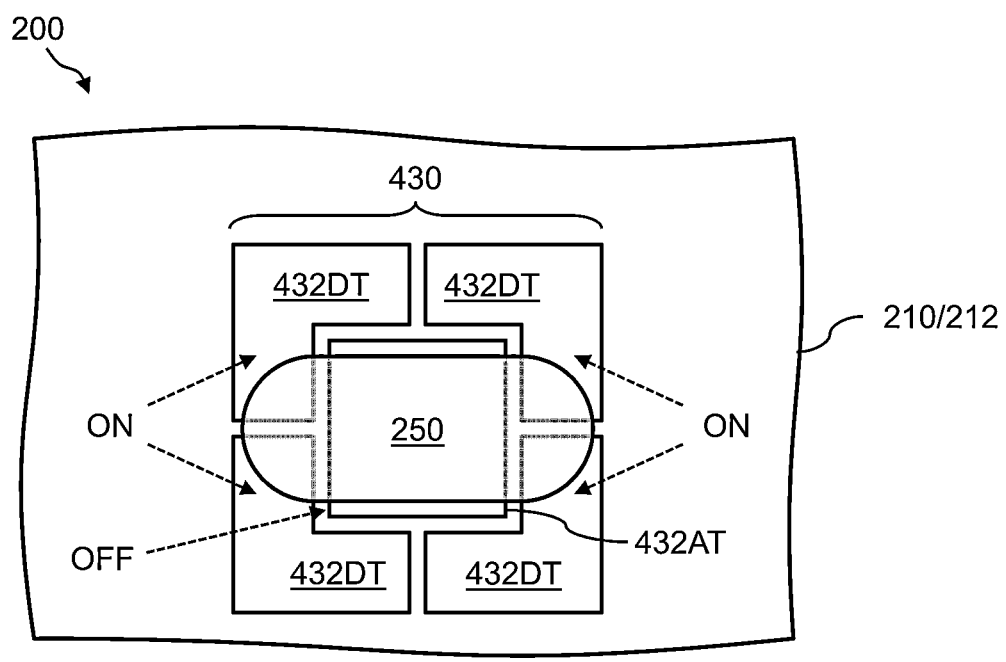
Figure 14:
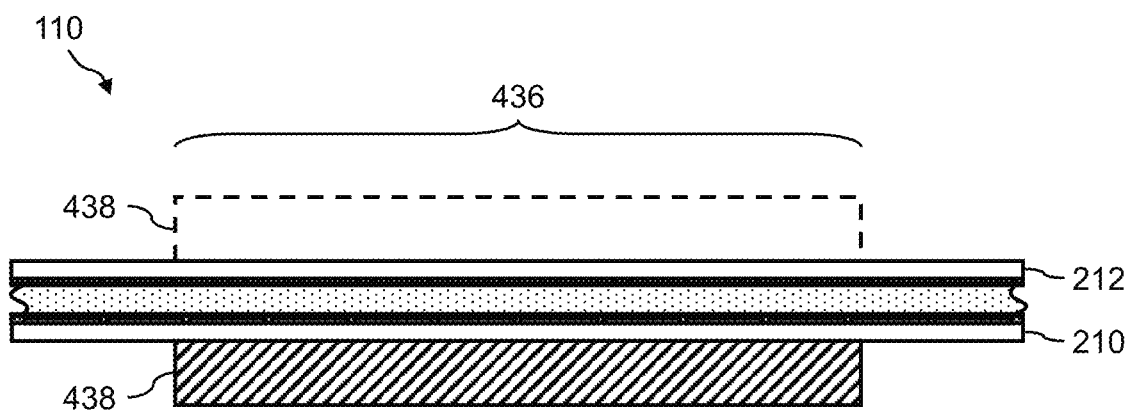
Figure 15A:
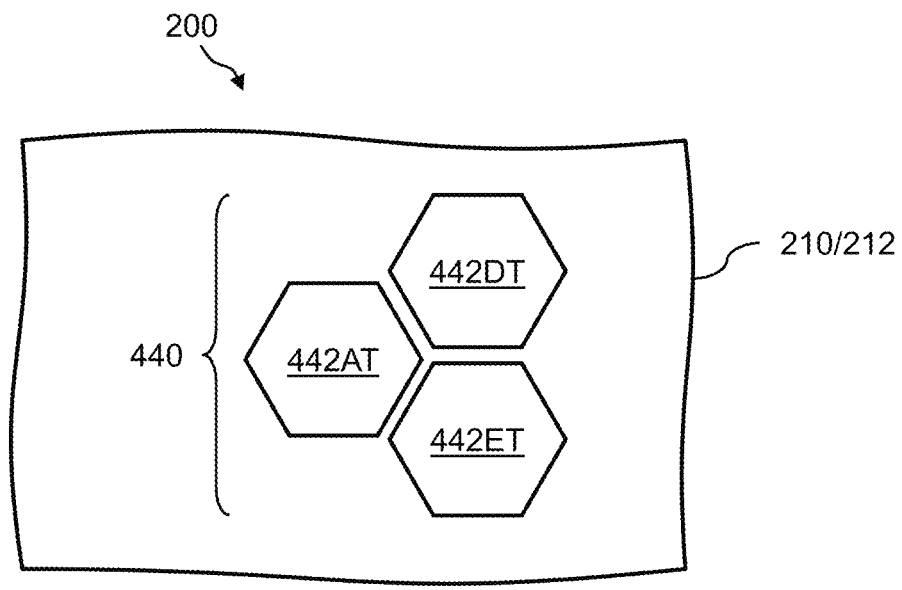
Figure 15B:
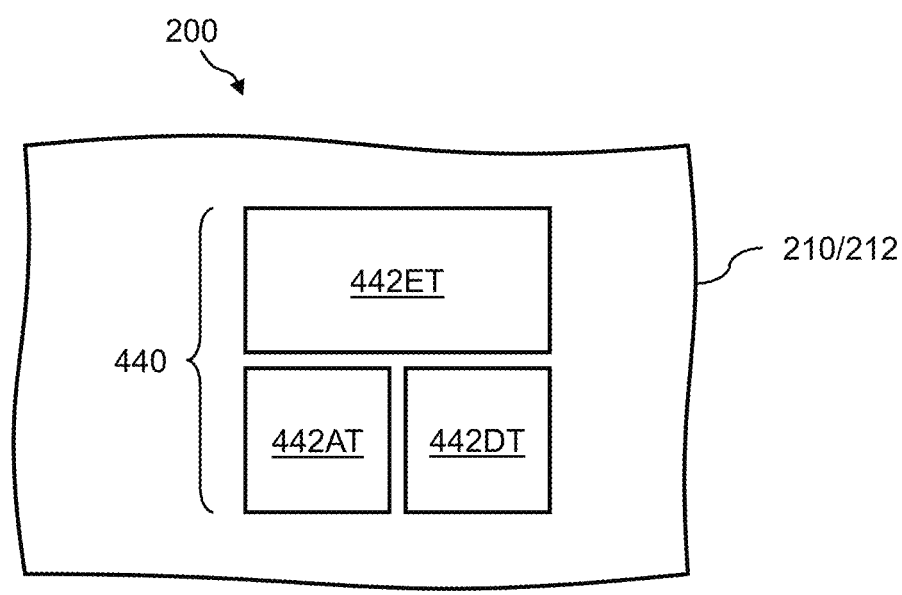
Figure 16A:
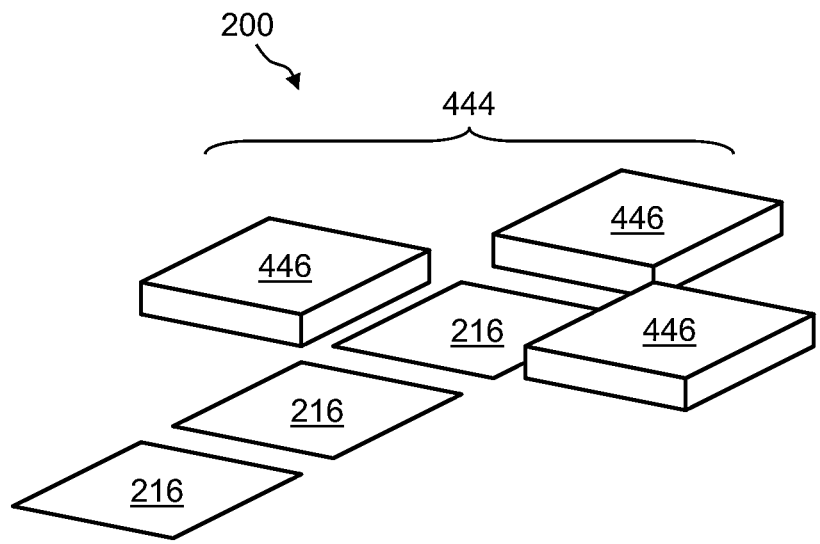
Figure 16B:
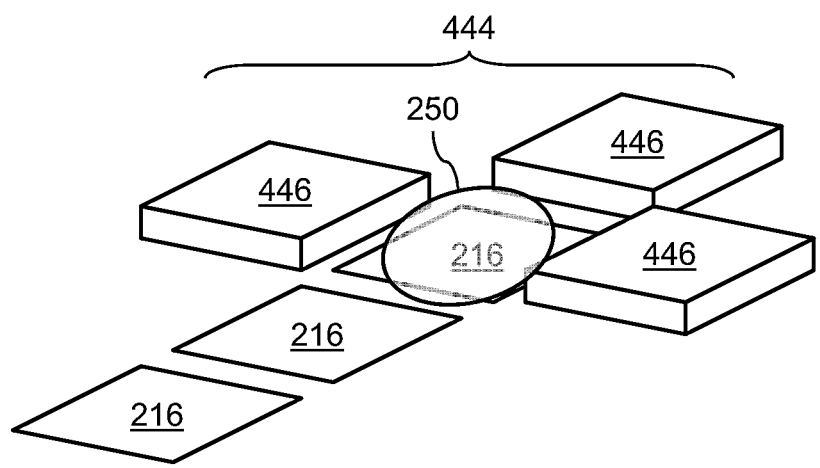
Figure 17A:
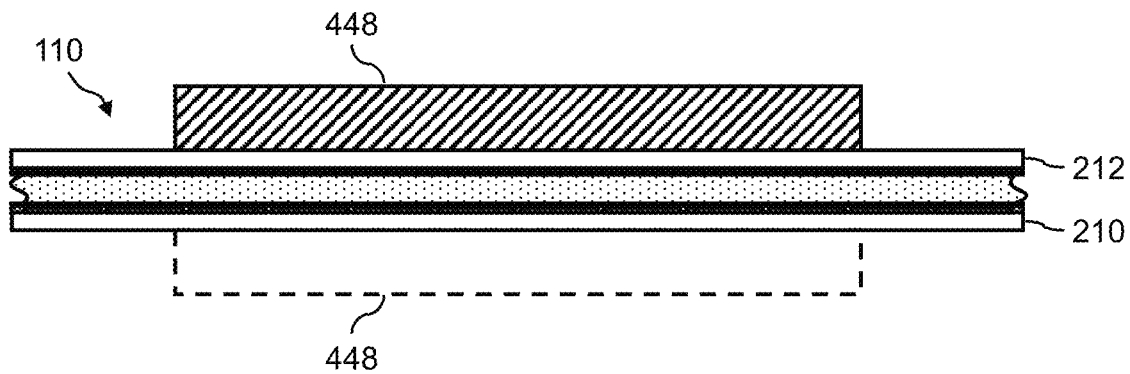
Figure 17B:
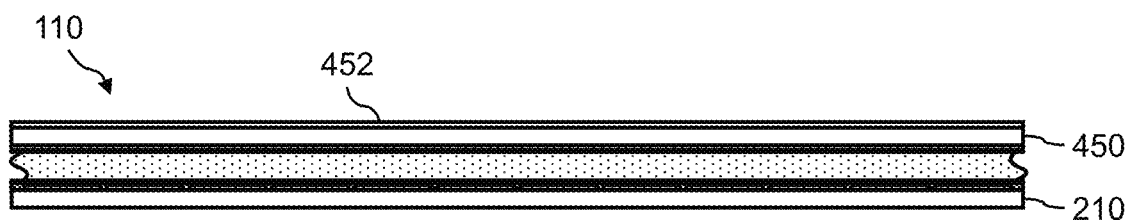
Figure 18:
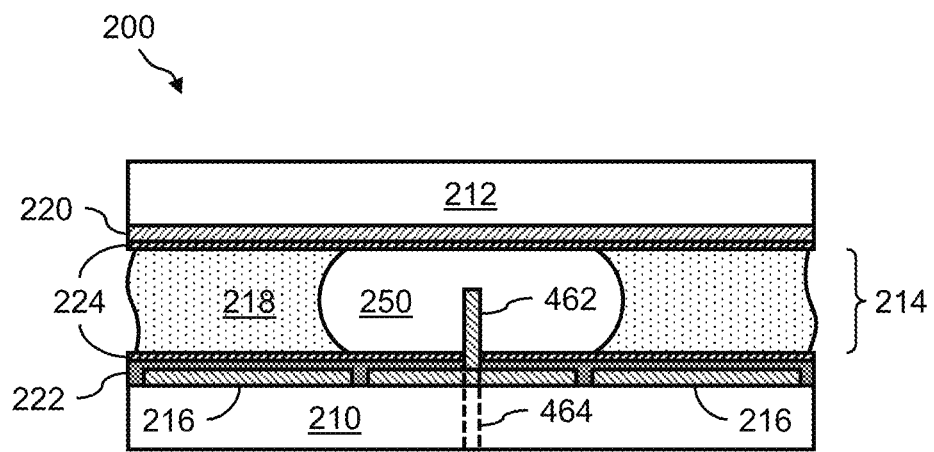
Figure 19:
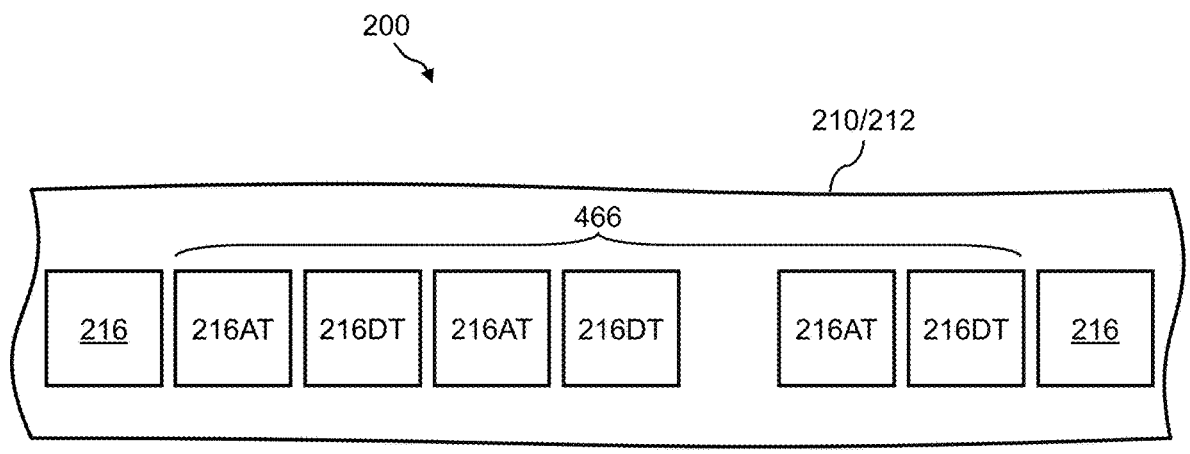
Figure 20A:
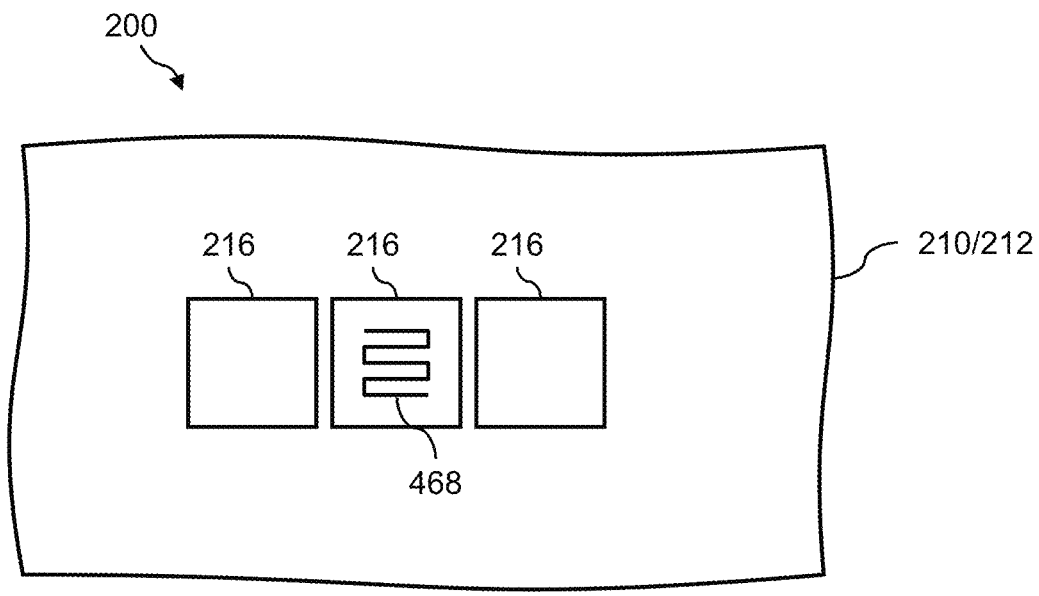
Figure 20B:
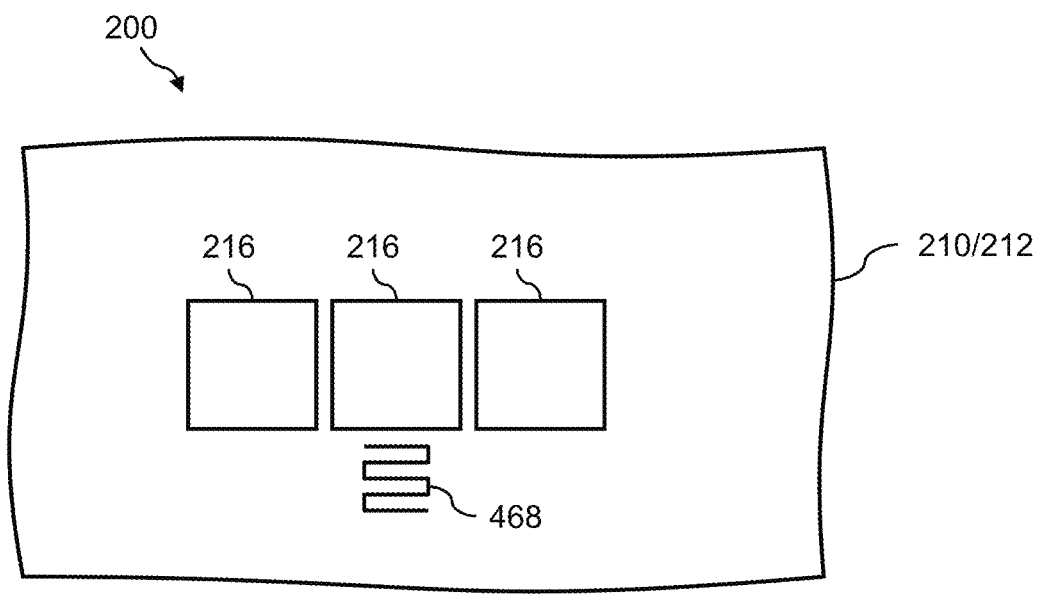
Figure 21:
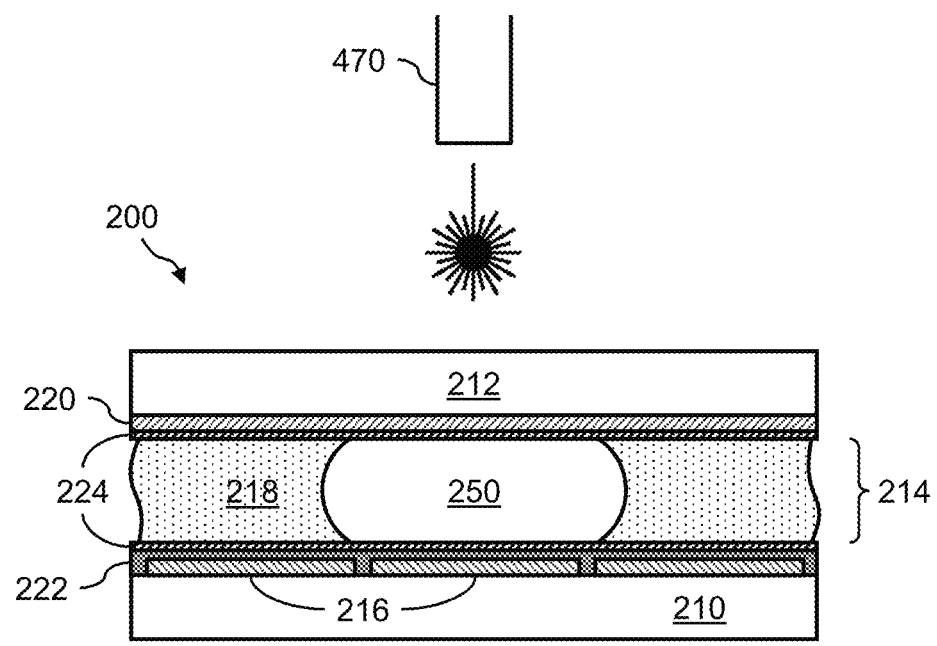
Figure 22:
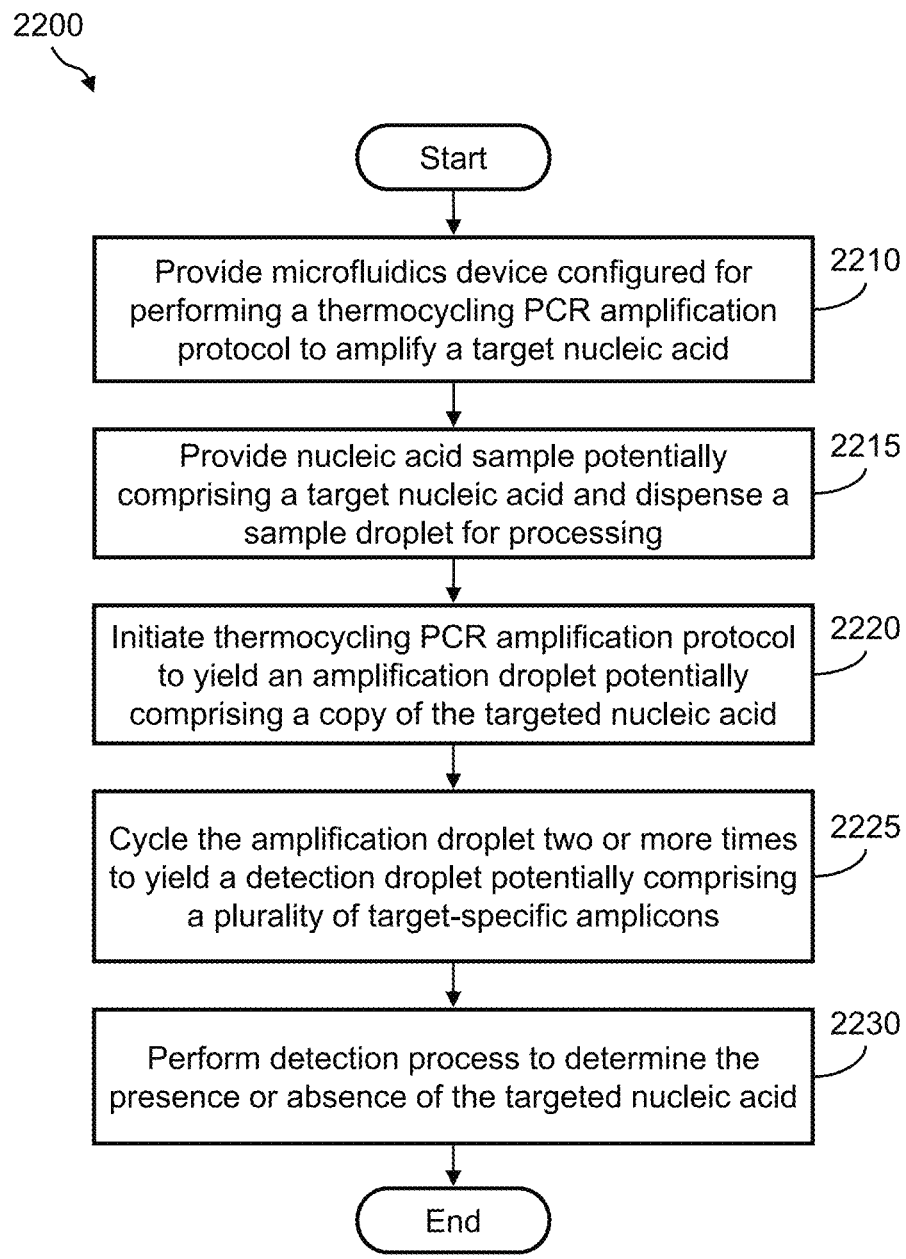
Figure 23:
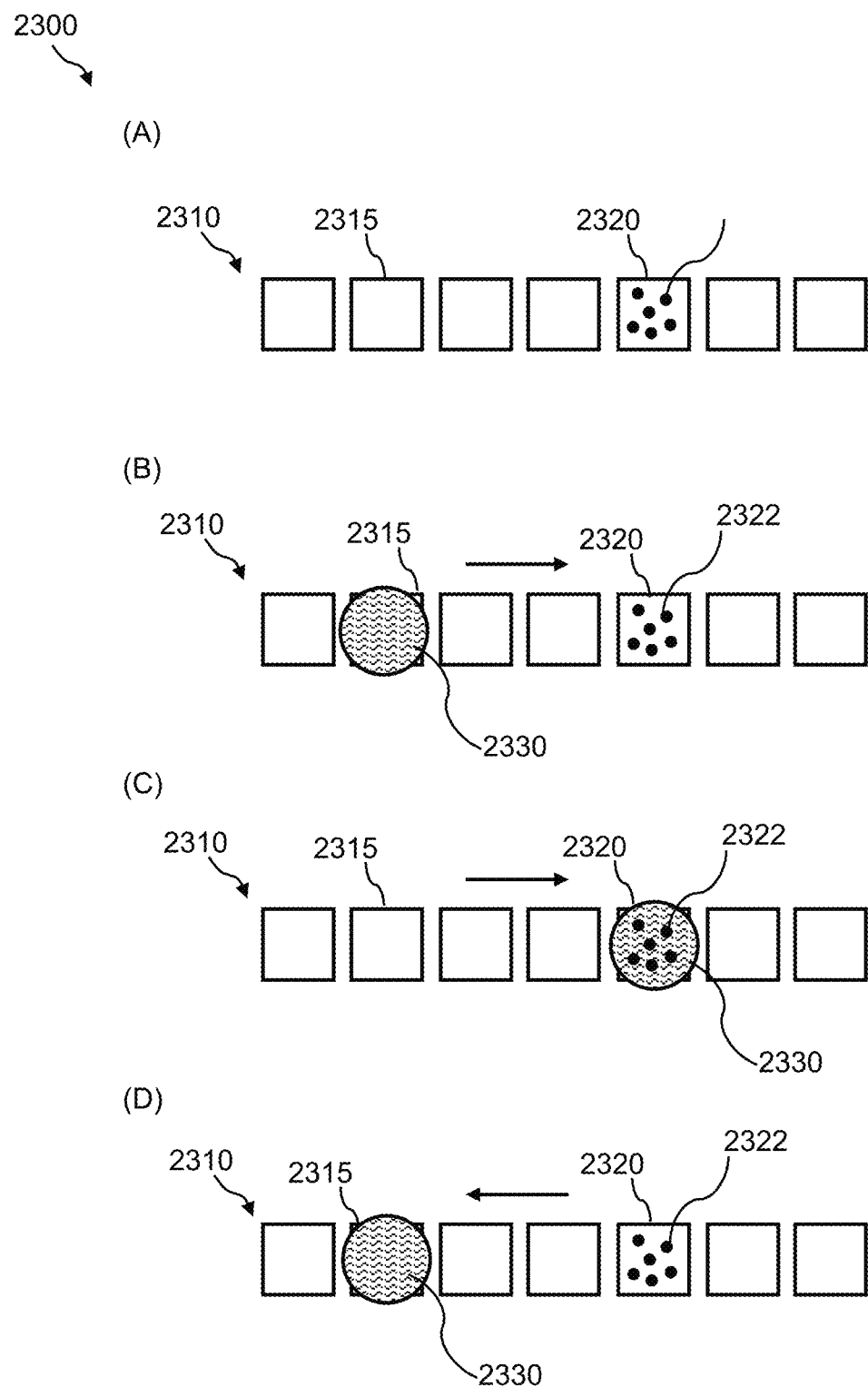
Figure 24:
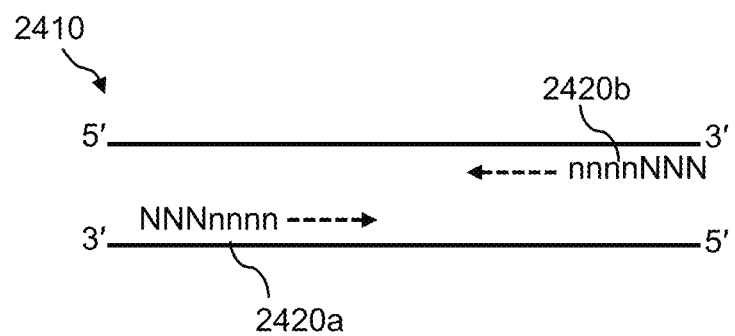
Figure 25A:
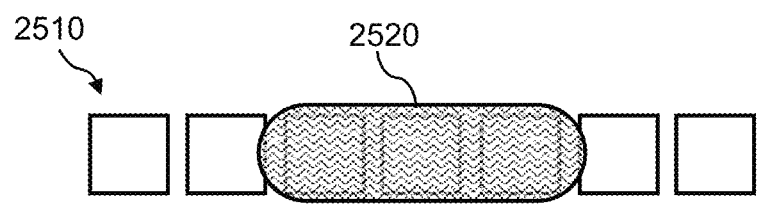
Figure 25B:
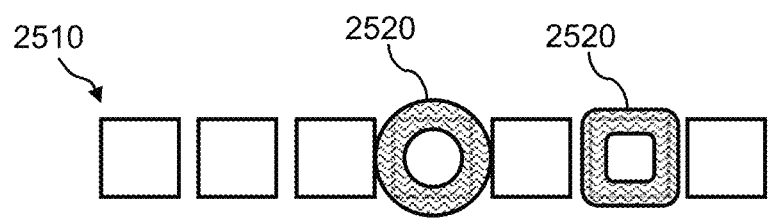
Figure 26A:
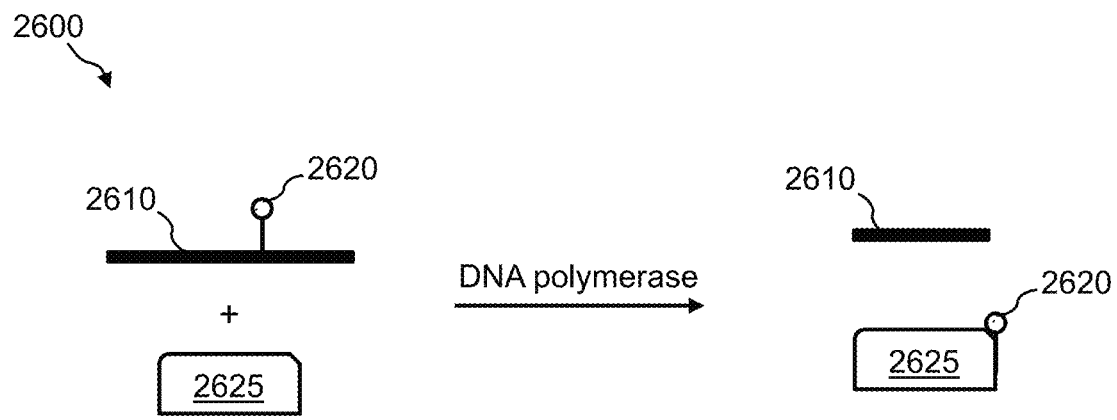
Figure 26B:
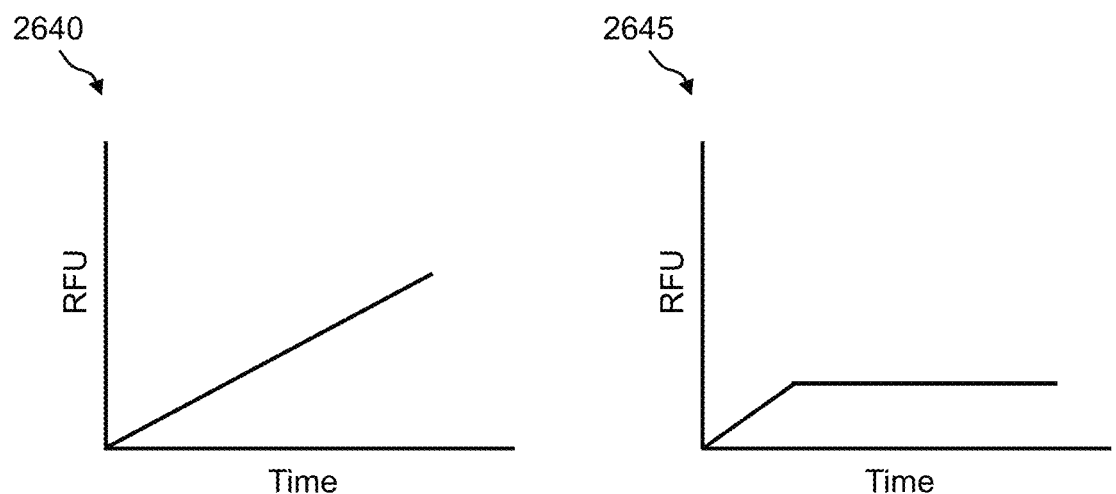
Figure 27A:
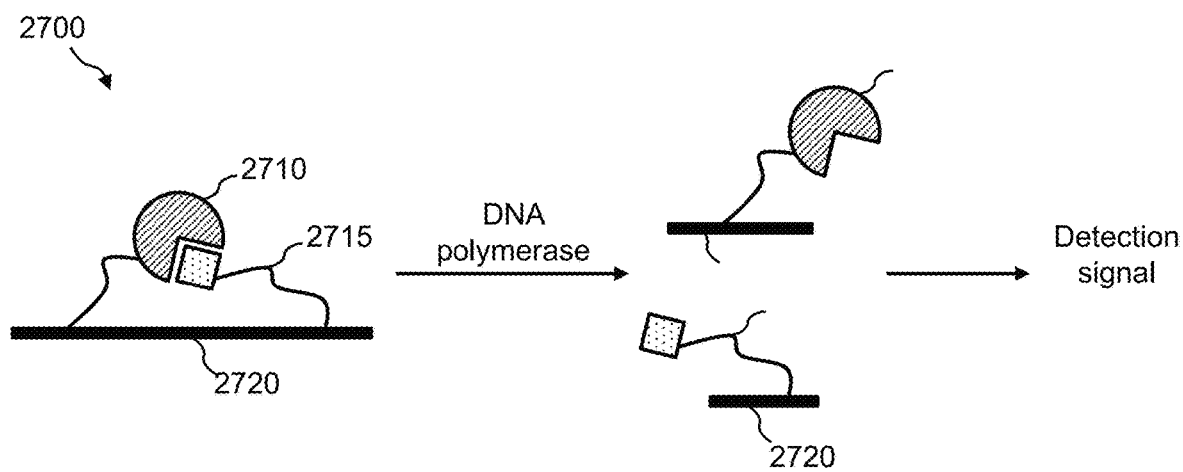
Figure 27B:
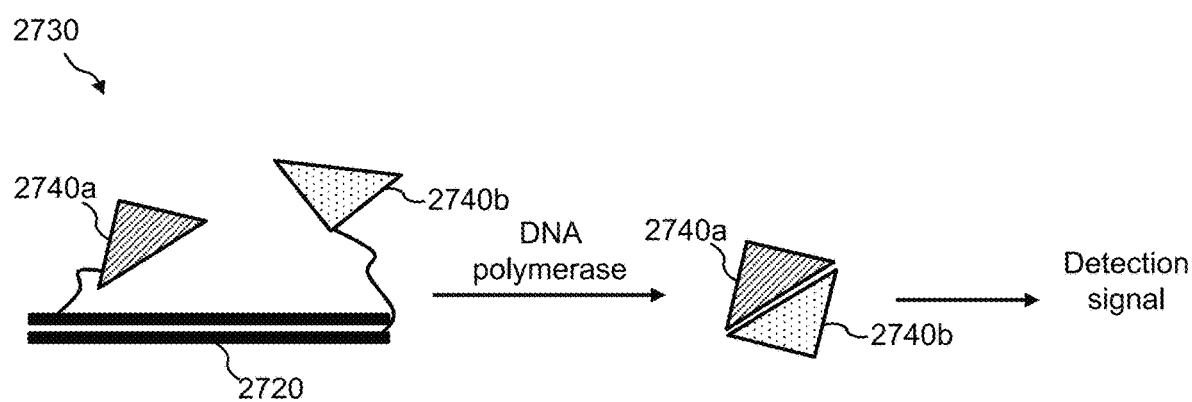

Having thus described the subject matter in general terms, reference will now be made to the accompanying drawings, which are not necessarily drawn to scale, and wherein:

FIG. 1 illustrates a block diagram of an example of a microfluidics system including thermal control mechanisms and/or techniques that support rapid PCR protocols, in accordance with an embodiment of the disclosure;

FIG. 2A and FIG. 2B illustrate a plan view and a cross-sectional view, respectively, of an example of a microfluidics structure, in accordance with an embodiment of the disclosure;

FIG. 3 illustrates a thermal cycling plot that shows an example of the droplet thermal cycling that may occur in, for example, a PCR protocol;

FIG. 4A and FIG. 4B illustrates plan views of a portion of the microfluidics structure shown in FIG. 2A and FIG. 2B and an example of a thermal zone for supporting rapid PCR protocols;

FIG. 5A and FIG. 5B illustrates a plan view and a cross-sectional view, respectively, of a portion of the microfluidics structure shown in FIG. 2A and FIG. 2B and another example of a thermal zone for supporting rapid PCR protocols and according to a simplest configuration;

FIG. 6A and FIG. 6B illustrate a plan view and a cross-sectional view, respectively, of a portion of the microfluidics structure shown in FIG. 2A and FIG. 2B and another example of a thermal zone for supporting rapid PCR protocols;

FIG. 7A and FIG. 7B illustrate a plan view and a cross-sectional view, respectively, of a portion of the microfluidics structure shown in FIG. 2A and FIG. 2B and another example of a thermal zone for supporting rapid PCR protocols;

FIG. 8A, FIG. 8B, and FIG. 8C illustrate plan views showing a process of using the electrode configuration shown in FIG. 7A and FIG. 7B;

FIG. 9A and FIG. 9B illustrate a plan view and a cross-sectional view, respectively, of a portion of the microfluidics structure shown in FIG. 2A and FIG. 2B and another example of a thermal zone for supporting rapid PCR protocols;

FIG. 10 illustrates a plan view of a portion of the microfluidics structure shown in FIG. 2A and FIG. 2B and another example of a thermal zone for supporting rapid PCR protocols;

FIG. 11A and FIG. 11B illustrate plan views of a portion of the microfluidics structure shown in FIG. 2A and FIG. 2B and another example of a thermal zone for supporting rapid PCR protocols;

FIG. 12A and FIG. 12B illustrate plan views of a portion of the microfluidics structure shown in FIG. 2A and FIG. 2B and another example of a thermal zone for supporting rapid PCR protocols;

FIG. 13A, FIG. 13B, and FIG. 13C illustrate plan views of a portion of the microfluidics structure shown in FIG. 2A and FIG. 2B and another example of a thermal zone for supporting rapid PCR protocols;

FIG. 14 illustrates a side view of a portion of the microfluidics structure shown in FIG. 2A and FIG. 2B and another example of a thermal zone for supporting rapid PCR protocols;

FIG. 15A and FIG. 15B illustrate plan views of a portion of the microfluidics structure shown in FIG. 2A and FIG. 2B and other examples of a thermal zone for supporting rapid PCR protocols;

FIG. 16A and FIG. 16B illustrate perspective views of a portion of the microfluidics structure shown in FIG. 2A and FIG. 2B and another example of a thermal control zone for supporting rapid PCR protocols;

FIG. 17A and FIG. 17B illustrate side views of a portion of the microfluidics structure shown in FIG. 2A and FIG. 2B and another example of a providing thermal control for supporting rapid PCR protocols;

FIG. 18 illustrates a cross-sectional view of a portion of the microfluidics structure shown in FIG. 2A and FIG. 2B and another example of a heating/sensing element for supporting rapid PCR protocols;

FIG. 19 illustrates a plan view of a portion of the microfluidics structure shown in FIG. 2A and FIG. 2B and another example of a thermal zone for supporting rapid PCR protocols;

FIG. 20A and FIG. 20B illustrate cross-sectional views of a portion of the microfluidics structure shown in FIG. 2A and FIG. 2B and examples of a sensing element for supporting rapid PCR protocols;

FIG. 21 illustrates a plan view of a portion of the microfluidics structure shown in FIG. 2A and FIG. 2B and an example of laser heating for supporting rapid PCR protocols;

FIG. 22 illustrates a flow diagram of an example of a method of optimizing a thermocycling PCR amplification protocol performed on a microfluidics device;

FIG. 23 illustrates a schematic diagram of an example of a process for maintaining the integrity of enzymes used in one or more process steps of a PCR protocol performed on a microfluidics device;

FIG. 24 illustrates a schematic diagram of an example of fast-cycling amplification primers;

FIG. 25A and FIG. 25B illustrate a schematic diagram of an example of an elongated droplet and a donut shaped droplet, respectively, that may be used to provide for more rapid and uniform heating of a reaction droplet during thermocycling on a microfluidics device;

FIG. 26A illustrates a schematic diagram of an example of an enzyme linked PCR process for real time detection of amplification products on a microfluidics device;

FIG. 26B illustrates a schematic diagram of a pair of plots showing representative negative and positive amplification results, respectively, for an enzyme-linked PCR process;

FIG. 27A illustrates a schematic diagram of an example of an enzyme-linked PCR process that uses a target-specific probe that includes an enzyme and enzyme inhibitor for real time detection of amplification products; and FIG. 27B illustrates a schematic diagram of an example of an enzyme-linked PCR process using a target specific probe that includes an inactive split enzyme for real time detection of amplification products.

DETAILED DESCRIPTION

The subject matter now will be described more fully hereinafter with reference to the accompanying drawings, in which some, but not all embodiments of the subject matter are shown. Like numbers refer to like elements throughout. The subject matter may be embodied in many different forms and should not be construed as limited to the embodiments set forth herein; rather, these embodiments are provided so that this disclosure will satisfy applicable legal requirements. Indeed, many modifications and other embodiments of the subject matter set forth herein will come to mind to one skilled in the art to which the subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims.

In some embodiments, the subject matter provides a microfluidics system, device, and methods for performing rapid polymerase chain reaction (PCR) protocols.

In some embodiments, the subject matter provides a microfluidics system including a microfluidics instrument housing a microfluidics cartridge (or device) along with any supporting components. Further, the microfluidics cartridge may be, for example, any fluidics device or cartridge, microfluidics device or cartridge, DMF device or cartridge, droplet actuator, flow cell device or cartridge, and the like.

In some embodiments, the microfluidics system, device, and methods provide thermal control mechanisms and/or techniques (1) at the microfluidics device level, and/or (2) in the assay protocol and/or reaction components.

In some embodiments, the microfluidics system, device, and methods provide a microfluidics cartridge including one or more thermal zones that may be any portion or portions of the microfluidics cartridge in which thermal cycling of a space and/or droplet occurs.

In some embodiments, the microfluidics system, device, and methods provide a microfluidics cartridge including one or more thermal zones with respect to PCR protocols that may include, for example, a denaturation temperature zone, an annealing temperature zone, an extension temperature zone, and the like.

In some embodiments, the microfluidics system, device, and methods provide a microfluidics cartridge including one or more thermal zones and wherein each of the thermal zones may include a droplet operations electrode thermally controlled to a denaturation temperature (DT) of, for example, from about 94° C. to about 98° C. and wherein this thermally controlled electrode may be called the DT electrode.

In some embodiments, the microfluidics system, device, and methods provide a microfluidics cartridge including one or more thermal zones and wherein each of the thermal zones may include a droplet operations electrode thermally controlled to an annealing temperature (AT) of, for example, from about 55° C. to about 60° C. and wherein this thermally controlled electrode may be called the AT electrode.

In some embodiments, the microfluidics system, device, and methods provide a microfluidics cartridge including one or more thermal zones and wherein each of the thermal zones may include a droplet operations electrode thermally controlled to an extension temperature (ET) of, for example, from about 68° C. to about 72° C. and wherein this thermally controlled electrode may be called the ET electrode.

In some embodiments, the microfluidics system, device, and methods provide a microfluidics cartridge including one or more thermal zones and wherein each of the thermal zones may include at least two or all three of the thermally controlled electrodes—the DT electrode, the AT electrode, and/or the ET electrode.

In some embodiments, the microfluidics system, device, and methods provide a microfluidics cartridge including one or more thermal zones and wherein each of the thermal zones may include at least two thermally controlled electrodes—the DT electrode, the AT electrode, and/or the ET electrode, and wherein the physical distance between the two electrodes is minimized to thereby minimize the number of droplet operations for moving a droplet therebetween and further to allow the droplet to be moved rapidly therebetween.

In some embodiments, the microfluidics system, device, and methods provide a microfluidics cartridge including one or more thermal zones and wherein each of the thermal zones may include at least two thermally controlled electrodes—the DT electrode, the AT electrode, and/or the ET electrode, and wherein the thermal conductivity between the two electrodes is minimized to provide a steep thermal gradient therebetween.

In some embodiments, the microfluidics system, device, and methods provide a microfluidics cartridge including one or more thermal zones and wherein each of the thermal zones may include at least two thermally controlled electrodes—the DT electrode, the AT electrode, and/or the ET electrode, and wherein the physical distance between the two electrodes is minimized and wherein the thermal conductivity between the two electrodes is minimized.

In some embodiments, the microfluidics system, device, and methods provide a microfluidics cartridge including one or more thermal zones and wherein each of the thermal zones may include at least two thermally controlled electrodes—the DT electrode, the AT electrode, and/or the ET electrode, and wherein a droplet shuttling method may include moving a droplet rapidly (via droplet operations) between the two closely placed electrodes and across the steep thermal gradient therebetween and thereby supporting rapid PCR protocols.

Referring now to FIG. 1 is a block diagram of an example of a microfluidics system 100 including thermal control mechanisms and/or techniques that support rapid PCR protocols, in accordance with an embodiment of the disclosure. In this example, microfluidics system 100 may include a microfluidics instrument 105. Further, microfluidics instrument 105 may house a microfluidics cartridge (or device) 110 along with any supporting components. Microfluidics cartridge 110 of microfluidics system 100 may be, for example, any fluidics device or cartridge, microfluidics device or cartridge, DMF device or cartridge, droplet actuator, flow cell device or cartridge, and the like. In various embodiments, microfluidics system 100 provides microfluidics cartridge 110 that may support automated processes to manipulate, process, and/or analyze biological materials.

Microfluidics cartridge 110 may be provided, for example, as a disposable and/or reusable device or cartridge. Microfluidics cartridge 110 may be used for processing biological materials. Generally, microfluidics cartridge 110 may facilitate digital microfluidics (DMF) capabilities for fluidic actuation including droplet transporting, merging, mixing, splitting, dispensing, diluting, agitating, deforming (shaping), and other types of droplet operations. Applications of these DMF capabilities may include, for example, sample preparation and waste removal. In one example, the DMF capabilities of microfluidics cartridge 110 of microfluidics system 100 may be used to perform assays, such as, but not limited to, PCR protocols. In microfluidics system 100, microfluidics cartridge 110 may be provided, for example, as a disposable and/or reusable cartridge.

In microfluidics instrument 105, the thermal control mechanisms and/or techniques may be provided with respect to microfluidics cartridge 110 of microfluidics system 100. The thermal control mechanisms and/or techniques may provide capability to execute rapid PCR protocols using microfluidics cartridge 110. Accordingly, the thermal control mechanisms and/or techniques may be provided (1) at the microfluidics device level, and/or (2) in the assay protocol and/or reaction components.

Also housed in fluidics instrument 105 of microfluidics system 100 may be a controller 112, a microfluidics interface 114, thermal control electronics 116, a thermal imaging camera 118, a detection system 120 further including an illumination source 122 and an optical measurement device 124.

Controller 112 may be electrically coupled to the various hardware components of microfluidics system 100, such as to microfluidics cartridge 110, thermal imaging camera 118, thermal control electronics 116, and illumination source 122 and optical measurement device 124 of detection system 120. In one example, controller 112 may be electrically coupled to microfluidics cartridge 110 via microfluidics interface 114 wherein the microfluidics interface 114 may be, for example, a pluggable interface for connecting mechanically and electrically to a microfluidics cartridge 110.

Controller 112 may, for example, be a general-purpose computer, special purpose computer, personal computer, tablet device, smartphone, smart watch, microprocessor, or other programmable data processing apparatus. Controller 112 may provide processing capabilities, such as storing, interpreting, and/or executing software instructions, as well as controlling the overall operations of microfluidics system 100. The software instructions may comprise machine-readable code stored in non-transitory memory that is accessible by controller 112 for the execution of the instructions. Controller 112 may be configured and programmed to control data and/or power aspects of these devices. For example, with respect to microfluidics cartridge 110, controller 112 may control droplet manipulation by activating and/or deactivating electrodes. Generally, controller 112 may be used for any functions of the microfluidics system 100. Further, controller 112 may include certain algorithms (not shown) for controlling any portions of microfluidics system 100.

Optionally, microfluidics instrument 105 may be connected to a network. For example, controller 112 may be in communication with a networked computer 140 via a network 142. Networked computer 140 may be, for example, any centralized server or cloud server. Network 142 may be, for example, a local area network (LAN) or wide area network (WAN) for connecting to the internet.

Further, microfluidics cartridge 110 may include one or more thermal zones 130. A thermal zone 130 may be any portion of microfluidics cartridge 110 in which thermal cycling of a space and/or droplet occurs. Thermal zones 130 may be designed to support rapid PCR protocols by incorporating, for example, steep temperature gradients that may be spanned rapidly in time. For example, one thermal zone 130 may be a denaturation temperature zone; another thermal zone 130 may be an annealing temperature zone; and yet another thermal zone 130 may be an extension temperature zone.

Additionally, each thermal zone 130 may include heaters 132 and/or thermal sensors 134. For example, the heaters 132 and/or thermal sensors 134 may be integrated into microfluidics cartridge 110 in relation to the droplet operations that occur therein. In one example, heaters 132 and thermal sensors 134 may be printed circuit board (PCB)-based heaters and PCB-based sensors, respectively, that may be integrated into, for example, a PCB-based substrate of microfluidics cartridge 110.

Thermal control electronics 116 may be provided for controlling the thermal aspects of microfluidics cartridge 110. Thermal control electronics 116 may include, for example, any thermal sensors for controlling heaters (e.g., Peltier elements and resistive heaters) and/or coolers arranged with respect to the microfluidics cartridge 110. Thermal control electronics 116 may be used for interfacing with the one or more heaters 132 and/or thermal sensors 134 that may be integrated into microfluidics cartridge 110. For example, thermal control electronics 116 may provide the drive circuitry for the integrated heaters 132 and the control circuitry for the integrated thermal sensors 134.

In microfluidics system 100, thermal imaging camera 118 and/or thermal sensors 134 may be used as thermal feedback mechanisms to controller 112 and/or to thermal control electronics 116. Thermal imaging camera 118 is a type of thermographic camera that renders infrared radiation as visible light. Thermal imaging cameras are used, for example, by firefighters to see areas of heat through smoke, darkness, or heat-permeable barriers. In microfluidics system 100, thermal imaging camera 118 may be, for example, the FLIR ETS320 camera available from FLIR Systems (Sweden) or the Fluke Ti40FT infrared camera (The Netherlands).

Detection system 120 may be, for example, an optical measurement system that includes illumination source 122 and optical measurement device 124. In this example, illumination source 122 and optical measurement device 124 may be arranged with respect to microfluidics cartridge 110. In one example, detection system 120 may be provided in relation to certain detection spots corresponding to the one or more thermal zones 130.

Illumination source 122 of detection system 120 may be, for example, a light source for the visible range (400-800 nm), such as, but not limited to, a white light-emitting diode (LED), a halogen bulb, an arc lamp, an incandescent lamp, lasers, and the like. Illumination source 122 is not limited to a white light source. Illumination source 122 may be any color light that is useful in microfluidics system 100. Optical measurement device 124 may be used to obtain light intensity readings. Optical measurement device 124 may be, for example, a charge coupled device, a photodetector, a spectrometer, a photodiode array, a digital camera (e.g., RGB color camera) or any combinations thereof. Further, microfluidics system 100 is not limited to one detection system 120 only (e.g., one illumination source 122 and one optical measurement device 124 only). Microfluidics system 100 may include multiple detection systems 120 (e.g., multiple illumination sources 122 and/or multiple optical measurement devices 124).

Referring now to FIG. 2A and FIG. 2B is a plan view and a cross-sectional view, respectively, of an example of a microfluidics structure 200. In one example, the formation of microfluidics cartridge 110 of microfluidics system 100 may be based generally on microfluidics structure 200. FIG. 2A shows that microfluidics structure 200 may include any arrangements (e.g., lines, paths, arrays) of droplet operations electrodes 216 (i.e., electrowetting electrodes).

FIG. 2B shows that microfluidics structure 200 may include a bottom substrate 210 and a top substrate 212 separated by a droplet operations gap 214. Droplet operations gap 214 may contain filler fluid 218, such as silicone oil or hexadecane. Bottom substrate 210 may be, for example, a silicon substrate or a PCB. Bottom substrate 210 may include an arrangement of droplet operations electrodes 216 (e.g., electrowetting electrodes). Droplet operations electrodes 216 may be formed, for example, of copper, gold, or aluminum. A dielectric layer 222 (e.g., parylene coating, silicon nitride) may be atop droplet operations electrodes 216. Top substrate 212 may be, for example, a glass or plastic substrate. Top substrate 212 may include a ground reference electrode 220. In one example, ground reference electrode 220 may be formed of indium tin oxide (ITO) and wherein ITO is substantially transparent to light. Further, a hydrophobic layer 224 may be provided on both the side of bottom substrate 210 and the side of top substrate 212 that is facing droplet operations gap 214. Examples of hydrophobic materials or coatings may include, but are not limited to, polytetrafluoroethylene (PTFE), Cytop, Teflon™ AF (amorphous fluoropolymer) resins, FluoroPel™ coatings, silane, and the like. Droplet operations may be conducted atop droplet operations electrodes 216 on a droplet operations surface. For example, droplet operations may be conducted atop droplet operations electrodes 216 with respect to a droplet 250 (droplet operations electrodes 216 and droplet 250 not drawn to scale).

Referring now to FIG. 3 is a thermal cycling plot 300 that shows an example of the droplet thermal cycling that may occur in, for example, a PCR protocol. Thermal cycling plot 300 shows a temperature curve 310. Temperature curve 310 begins with a rising temperature gradient 312 and reaching a denaturation temperature 314. Followed by a falling temperature gradient 316 and reaching a primer annealing temperature 318. Followed by a rising temperature gradient 320 and reaching a primer extension temperature 322.

In, for example, a typical PCR protocol, the denaturation temperature may be from about 94° C. to about 98° C. in one example or may be about 95° C. in another example. The annealing temperature may be from about 55° C. to about 60° C. in one example or may be about 60° C. in another example. The extension temperature may be from about 68° C. to about 72° C. in one example or may be about 70° C. in another example.

Generally, the denaturation temperature is a temperature sufficient to achieve denaturation. Likewise, the annealing temperature may be any temperature sufficient to achieve annealing. Likewise, the extension temperature may be any temperature sufficient to achieve extension. Further, in some cases the annealing and extension reactions may be performed at substantially the same temperature.

Reducing the overall processing time when using microfluidics may be beneficial. For example, reducing the overall processing may be of particular benefit in POC applications. The total processing time of, for example, a PCR protocol may be fully or in part dependent on the thermocycling rate or frequency. Accordingly, microfluidics system 100 includes thermal control mechanisms and/or techniques that support rapid PCR protocols. For example, the thermal control mechanisms and/or techniques of microfluidics system 100 may be used to shorten the rising and/or falling temperature gradient times, such as those shown in plot 300 of FIG. 3, as compared with standard PCR protocols performed using microfluidics.

Microfluidics Device-Level Structures and/or Components for Rapid Thermocycling Generally, one way of supporting rapid PCR protocols is to provide ways of rapid thermocycling. For example, steep temperature gradients allow two thermal zones to be provided physically close together, which allows the number of droplet operations to be minimized, thereby minimizing processing time. In a microfluidics device, thermal zones may be implemented via electrodes (e.g., droplet operations electrodes). Accordingly, minimizing the physical distance between, for example, the denaturation zone (e.g., about 95° C.), the extension zone (e.g., about 70° C.), and/or the annealing zone (e.g., about 60° C.) allows the number of droplet operations to be minimized, thereby minimizing processing time.

For example, the microfluidics device structures described below may include various electrode configurations that form thermal zones. In these examples, each of the thermal zones may include at least two of the thermally controlled electrodes—the DT electrode, the AT electrode, and/or the ET electrode. Further, the physical distance between the at least two thermally controlled electrodes is minimized. Further, the thermal conductivity between the at least two thermally controlled electrodes is minimized.

That is, to support rapid PCR protocols, the electrode configurations described below may be used to both (1) provide rapid droplet temperature transitions from one thermally controlled electrode to another (e.g., from the DT electrode to the AT electrode) and (2) provide rapid droplet movement (via droplet operations) from one thermally controlled electrode to another (e.g., from the DT electrode to the AT electrode).

With respect to providing rapid droplet temperature transitions, in one example and using heaters 132 and/or thermal sensors 134, a droplet at a DT electrode may be heated rapidly to the denaturation temperature (e.g., about 95° C.) within, for example, about 0.01 ms to about 10,00 ms. Then, in one example, the droplet may be moved (e.g., using one or two droplet operations) to, for example, an AT electrode. At the AT electrode, the droplet temperature transitions rapidly from the denaturation temperature (e.g., about 95° C.) to the annealing temperature (e.g., about 60° C.) within, for example, about 0.01 ms to about 1,000 ms. The various electrode configurations described below are designed to allow both rapid droplet temperature transitions and high speed shuttling between different thermally controlled electrodes.

Referring now to FIG. 4A and FIG. 4B is plan views of a portion of microfluidics structure 200 and an example of a thermal zone 400 for supporting rapid PCR protocols. For example, the design of thermal zone 400 may include a steep temperature gradient across which a droplet may be spanned rapidly in time using droplet operations.

Thermal zone 400 may be formed by a certain electrode configuration. For example, thermal zone 400 may include a droplet operations electrode 216 heated to a denaturation temperature (DT), hereafter called electrode 216DT. Further, electrode 216DT is an example of a DT electrode. In one example, electrode 216DT (i.e., the denaturation zone) may be set at about 95° C. Further, thermal zone 400 may include a droplet operations electrode 216 heated to an annealing temperature (AT), hereafter called electrode 216AT. Further, electrode 216AT is an example of an AT electrode. In one example, electrode 216AT (i.e., the annealing zone) may be set at about 60° C. These temperatures are exemplary only. Further, the space between electrode 216DT and electrode 216AT may from about 50 µm to about 200 µm in one example or about 100 µm in another example.

Further, an arrangement of multiple narrow droplet operations electrodes 402 may be provided between electrode 216DT and electrode 216AT. In the example shown in FIG. 4A, four (4) narrow droplet operations electrodes 402 may be provided between electrode 216DT and electrode 216AT. In one example, the footprint of the four narrow droplet operations electrodes 402 may be approximately the same as that of one droplet operations electrode 216. The width of each of the narrow droplet operations electrodes 402 may be, for example, about 75 µm, or about 100 µm, or about 125 µm, or about 250 µm. Additionally, the number and width of droplet operations electrodes 402 between electrode 216DT and electrode 216AT may vary. For example, FIG. 4B shows five (5) "wire" type droplet operations electrodes 402 between electrode 216DT and electrode 216AT.

In either case, electrode 216DT, electrode 216AT, and droplet operations electrodes 402 may be copper electrodes that have high thermal conductivity. However, each space or gap between the narrow or "wire" type droplet operations electrodes 402, which is absent copper, may have low thermal conductivity. Accordingly, the arrangement of multiple droplet operations electrodes 402 is provided to reduce or substantially prevent easy thermal conduction between electrode 216DT and electrode 216AT as compared with, for example, a full-sized droplet operations electrode 216 in place of droplet operations electrodes 402. This is because there is less copper and more gaps between electrode 216DT and electrode 216AT.

Accordingly, with electrode 216DT at one side of the droplet operations electrodes 402 and electrode 216DT at the opposite side of the droplet operations electrodes 402, a temperature gradient 404 exists between electrode 216DT and electrode 216AT. That is, temperature gradient 404 spans across the multiple narrow or "wire" type droplet operations electrodes 402. More specifically, a steep temperature gradient 404 of from about 95° C. to about 60° C. (or from about 60° C. to about 95° C.) may exist across a short distance that includes the multiple narrow droplet operations electrodes 402. Temperature gradient 404 may span a distance of from about 50 µm to about 200 µm in one example or about 100 µm in another example.

Electrode 216DT, electrode 216AT, and other droplet operations electrodes 216 are not within the temperature gradient 404. As such, these electrodes may be required to have both good electrical conductivity and good thermal conductivity. Accordingly, these electrodes may be formed, for example, of copper, gold, or aluminum. By contrast, the narrow or "wire" type droplet operations electrodes 402 are electrodes within the temperature gradient 404. As such, these electrodes may be required to have good electrical conductivity to facilitate droplet operations. However, these electrodes may not be required to have good thermal conductivity, which helps facilitate a good thermal gradient across these electrodes. Accordingly, these electrodes may be formed of materials that are good electrical conductors but poor thermal conductors. For example, the narrow or "wire" type droplet operations electrodes 402 may be formed of carbon, poly(3,4-ethylenedioxythiophene) (PEDOT), and the like. However, the narrow or "wire" type droplet operations electrodes 402 may be formed of copper, gold, or aluminum like electrode 216DT, electrode 216AT, and the other droplet operations electrodes 216.

Accordingly, droplet operations may occur rapidly in time across this short distance that includes the steep temperature gradient 404. That is, the arrangement of multiple narrow or "wire" type droplet operations electrodes 402 allows droplet operations to occur rapidly in time between electrode 216DT (i.e., the denaturation zone) and electrode 216AT (i.e., the annealing zone), thereby supporting rapid PCR protocols.

Referring now to FIG. 5A and FIG. 5B is a plan view and a cross-sectional view, respectively, of a portion of the microfluidics structure 200 and an example of a thermal zone 406 for supporting rapid PCR protocols and according to a simplest configuration. Thermal zone 406 may be substantially the same as thermal zone 400 shown in FIG. 4A and FIG. 4B except that thermal zone 406 is absent the multiple droplet operations electrodes 402. That is, the multiple droplet operations electrodes 402 of thermal zone 400 are replaced with an electrode gap 408 having no electrodes. That is, in this example, electrode gap 408 is between electrode 216DT and electrode 216AT. Further, no electrodes are provided within the space of electrode gap 408. Therefore, electrode gap 408 provides a region of low thermal conductivity (or of high thermal insulation) between electrode 216DT and electrode 216AT. Accordingly, a temperature gradient 412 may form across electrode gap 408. That is, a steep temperature gradient 412 of from about 95° C. to about 60° C. (or from about 60° C. to about 95° C.) may form between electrode 216DT and electrode 216AT. In this example, the temperature gradient 412 may be modulated by sizing the electrode gap 408 between electrode 216DT and electrode 216AT.

The size of electrode gap 408 may be from about 50 µm to about 200 µm in one example or may be about 100 µm in another example. The electrode gap 408 may be larger than the typical gap or space between, for example, droplet operations electrodes 216. Accordingly, this electrode configuration may require a larger electrowetting voltage to move a droplet from, for example, electrode 216DT to electrode 216AT than is required to move a droplet along a line of droplet operations electrodes 216. Generally, to ensure reliable droplet operations, the electrowetting voltage value may vary depending on the size of electrode gap 408.

Referring now to FIG. 6A and FIG. 6B is a plan view and a cross-sectional view, respectively, of a portion of microfluidics structure 200 and another example of thermal zone 406 for supporting rapid PCR protocols. For example, the design of thermal zone 406 may include the steep temperature gradient 412 that may be spanned rapidly in time using droplet operations. Here, thermal zone 412 may be substantially the same as thermal zone 412 shown in FIG. 5A and FIG. 5B except for the presence of an indentation (or divot) 410 between electrode 216DT and electrode 216AT.

Generally, the absence of any copper (e.g., electrodes) between electrode 216DT and electrode 216AT forms a natural depression in both dielectric layer 222 and hydrophobic layer 224 that are atop bottom substrate 210. In this way, indentation 410 is provided in the electrode gap 408 between electrode 216DT and electrode 216AT. Further, electrode gap 408 with indentation 410 provides a region of low thermal conductivity (or of high thermal insulation) between electrode 216DT and electrode 216AT. In one example, the footprint of the indentation 410 may be approximately the same as or smaller than that of one droplet operations electrode 216.

Because of the presence of indentation 410, the droplet operations gap 214 is greater within electrode gap 408 than outside of electrode gap 408 at the droplet operations electrodes 216, as shown in FIG. 6B. In digital microfluidics, when there is no electrowetting voltage present a droplet will move (passively) to the larger gap area (i.e., lowest pressure area). This may be a typical characteristic of standard capillary forces on hydrophobic surfaces. Accordingly, indentation 410 provides a natural landing place for droplets when no electrowetting voltage is present. For example, a droplet (not shown) may be atop either electrode 216DT or electrode 216AT. Then when both electrode 216DT and electrode 216AT are turned off, the droplet will move by capillary forces to indentation 410, which is between electrode 216DT or electrode 216AT.

Again, with electrode 216DT at one side of electrode gap 408 with indentation 410 and electrode 216DT at the opposite side, the temperature gradient 412 exists between electrode 216DT and electrode 216AT and across the electrode gap 408 with indentation 410. More specifically, a steep temperature gradient 412 of from about 95° C. to about 60° C. (or from about 60° C. to about 95° C.) may exist across a short distance that includes electrode gap 408 with indentation 410. Again, the temperature gradient 412 may be modulated by sizing the electrode gap 408 and indentation 410 between electrode 216DT and electrode 216AT.

Accordingly, droplet operations may occur rapidly in time across this short distance that includes the steep temperature gradient 412. That is, the presence of electrode gap 408 with indentation 410 allows droplet operations to occur rapidly in time between electrode 216DT (i.e., the denaturation zone) and electrode 216AT (i.e., the annealing zone), thereby supporting rapid PCR protocols.

Referring now to FIG. 7A and FIG. 7B is a plan view and a cross-sectional view, respectively, of a portion of microfluidics structure 200 and an example of a thermal zone 454 for supporting rapid PCR protocols. For example, the design of thermal zone 454 may include a steep temperature gradient that may be spanned rapidly in time using droplet operations. Thermal zone 454 may be formed by a certain electrode configuration. For example, thermal zone 454 may include electrode 216DT (i.e., the denaturation zone) and the electrode 216AT (i.e., the annealing zone).

Further, the electrode gap 408 may be provided between electrode 216DT and electrode 216AT. The presence of electrode gap 408 provides the temperature gradient 412 between electrode 216DT and electrode 216AT. For example, a steep temperature gradient 412 of from about 95° C. to about 60° C. (or from about 60° C. to about 95° C.) may exist across electrode gap 408. The electrode configuration of electrode 216AT and electrode 216DT with electrode gap 408 therebetween provides a short path across a steep temperature gradient by which droplets may be shuttled in, for example, a PCR protocol. In this example, the temperature gradient 412 may be modulated by sizing the electrode gap 408 between electrode 216DT and electrode 216AT. Again, electrode gap 408 may be from about 50 μm to about 200 μm in one example or may be about 100 μm in another example.

Further, FIG. 7B shows that there may be no copper in electrode gap 408 between electrode 216AT and electrode 216DT. Accordingly, indentation 410 may be present in the topology of the droplet operations surface. In the case in which both electrode 216DT and electrode 216AT are deactivated (both OFF), a droplet may naturally migrate by capillary forces to indentation 410 between electrode 216DT and electrode 216AT, as shown, for example, in FIG. 8A, FIG. 8B, and FIG. 8C.

To further ensure that a droplet will move to indentation 410 when both electrode 216DT and electrode 216AT are deactivated (both OFF), physical barriers 461 may be provided with respect to electrode 216AT and electrode 216DT. For example, one C-shaped physical barrier 461 may be provided near electrode 216AT. Another C-shaped physical barrier 461 may be provided near electrode 216DT. Physical barriers 461 may be, for example, raised copper traces with respect to the plane of droplet operations electrodes 216.

Referring now to FIG. 8A, FIG. 8B, and FIG. 8C is plan views showing a process of using the electrode configuration shown in FIG. 7A and FIG. 7B. For example, FIG. 8A shows an example of electrode 216AT activated (ON) and electrode 216DT deactivated (OFF). Therefore, droplet 250 sits atop electrode 216AT. Similarly, FIG. 8B shows an example of electrode 216AT deactivated (OFF) and electrode 216DT activated (ON). Therefore, droplet 250 sits atop electrode 216DT. However, when both electrode 216AT and electrode 216DT are deactivated (OFF) then droplet 250 tends to automatically move to indentation 410 in the electrode gap 408 between electrode 216AT and electrode 216DT. Further, in the process steps above, physical barriers 461 ensure that droplet 250 can only move between electrode 216AT and electrode 216DT.

FIG. 9A and FIG. 9B illustrate a plan view and a cross-sectional view, respectively, of a portion of the microfluidics structure 200 and another example of a thermal zone 456 for supporting rapid PCR protocols. In this configuration, an opening or through-hole 458 may be provided in bottom substrate 210. For example, opening or through-hole 458 is provided within the electrode gap 408 between electrode 216AT and electrode 216DT. Further, no electrode is provided within the electrode gap 408 between electrode 216AT and electrode 216DT.

The purpose of opening or through-hole 458 in bottom substrate 210 is to provide a region of low thermal conductivity (or high thermal insulation). Using opening or through-hole 458, a temperature gradient 460 may be formed between electrode 216AT and electrode 216DT.

Opening or through-hole 458 may be filled with air or any other thermal insulating material suitable for use in a microfluidics environment.

FIG. 10 is a plan view showing another configuration using openings or through-holes 458 to form regions of low thermal conductivity and therefore form temperature gradients. In one example, a certain electrode, such as electrode 216AT, may be surrounded with a circular pattern of openings or through-holes 458 in bottom substrate 210. Again, openings or through-holes 458 may be filled with air or any other thermal insulating material suitable for use in a microfluidics environment.

The presence of openings or through-holes 458 as shown, for example, in FIG. 9A, FIG. 9B, and FIG. 10, is not limited to bottom substrate 210 only. Openings or through-holes 458 may be provided in bottom substrate 210 only, top substrate 212 only, or both bottom substrate 210 and top substrate 212.

Referring now to FIG. 11A and FIG. 11B is plan views of a portion of microfluidics structure 200 and an example of a thermal zone 414 for supporting rapid PCR protocols. For example, the design of thermal zone 414 may include a steep temperature gradient that may be spanned rapidly in time using droplet operations. Thermal zone 414 may be formed by a certain electrode configuration. For example, thermal zone 414 may include a triangular electrode 416DT (i.e., the denaturation zone) and a triangular electrode 416AT (i.e., the annealing zone). Triangular electrodes 416DT and 416AT may be arrange in opposing fashion as shown. That is, the wide end of triangular electrode 416DT is arranged with respect to the narrow end of triangular electrode 416AT and vice versa. Further, triangular electrode 416DT is an example of a DT electrode. Likewise, triangular electrode 416AT is an example of an AT electrode.

In, for example, a PCR protocol, a droplet, such as droplet 250, may be shuttled back and forth across triangular electrodes 416DT and 416AT. For example, FIG. 11A shows triangular electrode 416DT (i.e., at about 95° C.) is activated (ON) and triangular electrode 416AT (i.e., at about 60° C.) is deactivated (OFF). In this state, the majority of droplet 250 may sit atop the wide end and largest area of triangular electrode 416DT for denaturation. Albeit a small portion of droplet 250 may sit atop a negligible portion of triangular electrode 416AT, which may be at about 60° C. That is, droplet 250 has a large amount of overlap with triangular electrode 416DT and a small amount of overlap with triangular electrode 416AT.

Next, FIG. 11B shows triangular electrode 416DT (i.e., at about 95° C.) is deactivated (OFF) and triangular electrode 416AT (i.e., at about 60° C.) is activated (ON). This causes droplet 250 to move across thermal zone 414. In this state, the majority of droplet 250 may now sit atop the wide end and largest area of triangular electrode 416AT for annealing. Albeit a small portion of droplet 250 may sit atop a negligible portion of triangular electrode 416DT, which may be at about 95° C. That is, droplet 250 now has a small amount of overlap with triangular electrode 416DT and a large amount of overlap with triangular electrode 416AT. Droplet shuttling may occur by switching ON and OFF the triangular electrodes 416DT and 416AT in alternating fashion.

Accordingly, this arrangement of triangular electrodes 416DT and 416AT provides a temperature gradient 418 along the length thereof. More specifically, a steep temperature gradient 418 of from about 95° C. to about 60° C. (or from about 60° C. to about 95° C.) may exist along this length. In this example, the temperature gradient 418 may be modulated by sizing this arrangement of triangular electrodes 416DT and 416AT. In this arrangement, triangular electrodes 416DT and 416AT may essentially take up one electrode space. Yet, the droplet may be shuttled between two heating zones.

Referring now to FIG. 12A and FIG. 12B is plan views of a portion of microfluidics structure 200 and an example of a thermal zone 420 for supporting rapid PCR protocols. For example, the design of thermal zone 420 may include a steep temperature gradient that may be spanned rapidly in time using droplet operations. Thermal zone 420 may be formed by a certain electrode configuration. For example, FIG. 12A shows that thermal zone 420 may include an elongated electrode 422. One end of elongated electrode 422 may be set at DT (i.e., the denaturation zone). The opposite end of elongated electrode 422 may be set at AT (i.e., the annealing zone).

Accordingly, elongated electrode 422 provides a temperature gradient 424 along its length. More specifically, a steep temperature gradient 424 of from about 95° C. to about 60° C. (or from about 60° C. to about 95° C.) may exist along its length. In this example, the temperature gradient 424 may be modulated by sizing elongated electrode 422. The length of elongated electrode 422 may be, for example, from about 50 μm to about 200 μm.

Next, FIG. 12B shows an elongated droplet 250 sitting atop elongated electrode 422. Accordingly, one end of elongated droplet 250 will heat to DT (e.g., about 95° C.). the other end of elongated droplet 250 will heat to AT (e.g., about 60° C.). In so doing, convection heating may occur within the volume of elongated droplet 250 causing certain circulating flow 426 to occur therein. With this circulating flow 426 passing through both the DT- and AT-portions of elongated droplet 250, PCR protocols may occur therein.

Referring now to FIG. 13A, FIG. 13B, and FIG. 13C is plan views of a portion of microfluidics structure 200 and an example of a thermal zone 430 for supporting rapid PCR protocols. For example, the design of thermal zone 430 may include a steep temperature gradient that may be spanned rapidly in time using droplet operations. Thermal zone 430 may be formed by a certain electrode configuration. For example, FIG. 13A shows that the electrode configuration of thermal zone 430 may include an electrode 432AT (i.e., the annealing zone) surrounded by an arrangement of multiple electrodes 432DT (i.e., the denaturation zone). Essentially, electrode 432AT is flanked on all sides by the multiple electrodes 432DT. Electrode 432AT is an example of an AT electrode. Each electrode 432DT is an example of a DT electrode. In another example, the multiple electrodes 432DT may be one continuous electrode 432DT (not shown) surrounding electrode 432AT.

In an example of using thermal zone 430, FIG. 13B shows electrode 432AT (i.e., at about 60° C.) is activated (ON) and the multiple electrodes 432DT (i.e., at about 95° C.) are deactivated (OFF). Thus, droplet 250 sits atop electrode 432AT and reaches about 60° C. Then, FIG. 13C shows the multiple electrodes 432DT (i.e., at about 95° C.) are activated (ON) and electrode 432AT (i.e., at about 60° C.) is deactivated (OFF). As a result, and because the multiple electrodes 432DT flank electrode 432AT, droplet 250 stretches onto the flanking electrodes 432DT and reaches about 95° C. Thermocycling of droplet 250 may occur rapidly back and forth according to FIG. 13B and FIG. 131C.

In another example, electrodes 432DT and electrode 432AT may be swapped. For example, the electrode configuration of thermal zone 430 may include an electrode 432DT (i.e., the denaturation zone) surrounded by an arrangement of multiple electrodes 432AT (i.e., the annealing zone Accordingly, this arrangement of multiple electrodes 432DT around electrode 432AT provides a temperature gradient 434 from about the center of electrode 432AT to the outer perimeter of electrodes 432DT. More specifically, a steep temperature gradient 434 of from about 95° C. to about 60° C. (or from about 60° C. to about 95° C.) may exist radially around the electrode configuration of thermal zone 430. The close proximity of the electrode 432AT and electrode 432DT provides a short path by which droplets may be shuttled in, for example, a PCR protocol.

Referring now to FIG. 14 is a side view of a portion of microfluidics cartridge 110 and an example of a thermal zone 436 for supporting rapid PCR protocols. In this example, a heatsink 438 may be provided with respect to thermal zone 436 of microfluidics structure 200. Heatsink 438 may be, for example, an active heatsink, a heatsink formed of parylene-C copper, and the like. Heatsink 438 may be provided on bottom substrate 210 only, on top substrate 212 only, or on both bottom substrate 210 and top substrate 212.

With respect to supporting rapid PCR protocols, heatsink 438 may be used to increase the speed at which heat can be removed from the ambient air surrounding microfluidics structure 200. This allows creation of a steep temperature gradient within a short distance at thermal zone 436.

Referring now to FIG. 15A and FIG. 15B is plan views of a portion of microfluidics structure 200 and examples of a thermal zone 440 for supporting rapid PCR protocols. In one example, FIG. 15A shows an electrode configuration including three hexagon-shaped droplet operations electrodes. For example, a hexagonal electrode 442AT for providing the annealing temperature (i.e., at about 60° C.), a hexagonal electrode 442ET for providing the extension temperature (i.e., at about 70° C.), and a hexagonal electrode 442DT for providing the denaturation temperature (i.e., at about 95° C.). A hexagonal electrodes 442AT, 442ET, and 442DT may be arranged in close proximity as shown. Hexagonal electrode 442AT is an example of an AT electrode. Hexagonal electrode 442ET is an example of an ET electrode. Hexagonal electrode 442DT is an example of a DT electrode. In this example, a typical sequence may be a droplet at hexagonal electrode 442DT, then at hexagonal electrode 442AT, then at hexagonal electrode 442ET, and then continue looping.

Thermal zone 440 is not limited to hexagon-shaped electrodes. Other shapes are possible, such as, but not limited to, square, offset squares, rectangular, triangular, circular, and the like. For example, in FIG. 15B, thermal zone 440 may include an arrangement of square and rectangular electrodes. In this example, a square electrode 442AT and a square electrode 442DT are arranged with respect to a rectangular electrode 442ET.

In both of the examples shown in FIG. 15A and FIG. 15B, the temperature gradients between electrodes 442AT, 442ET, and 442DT may be modulated by the size, shape, and spacing of the electrodes. Because of the close proximity of electrodes 442AT, 442ET, and 442DT to each other, a steep temperature gradient may exist from any one to the other two.

With respect to supporting rapid PCR protocols, in some protocols, droplet operations may occur that include all three electrodes, such as transporting a droplet (not shown) from electrode 442AT (i.e., at about 60° C.), then to electrode 442ET (i.e., at about 70° C.), and then to electrode 442DT (i.e., at about 95° C.). In another example, droplet operations may occur that include two electrodes, such as transporting a droplet (not shown) from electrode 442AT (i.e., at about 60° C.) and then to electrode 442DT (i.e., at about 95° C.). In this example, skipping electrode 442ET (i.e., at about 70° C.).

Further, the electrode configurations of thermal zone 440 shown in FIG. 15A and FIG. 15B may allow minimizing the droplet time at electrode 442AT (i.e., at about 60° C.) and electrode 442DT (i.e., at about 95° C.), while maximizing the droplet time at electrode 442ET (i.e., at about 70° C.).

Further, a benefit of the electrode arrangements of thermal zone 440 shown in FIG. 15A and FIG. 15B is that the electrodes 442AT, 442ET, and 442DT may be positioned close together. Therefore, a droplet may be moved quickly (via droplet operations) from one electrode to the next for supporting rapid PCR protocols.

Referring now to FIG. 16A and FIG. 16B is perspective views of a portion of microfluidics structure 200 and an example of a thermal control zone 444 for supporting rapid PCR protocols. In this example, multiple heating electrodes 446 may be arranged with respect to a certain droplet operations electrode 216. Heating electrodes 446 may be an example of heaters 132 (e.g., integrated PCB-based heaters) shown and described in FIG. 1. Heating electrodes 446 may be, for example, raised copper electrodes with respect to the plane of droplet operations electrodes 216.

In one example, the droplet operations electrode 216 may be flanked on three sides with heating electrodes 446, as shown in FIG. 16A and FIG. 16B. In another example, the droplet operations electrode 216 may be flanked on two sides with heating electrodes 446. In yet another example, the droplet operations electrode 216 may be flanked on one side with a heating electrode 446.

In the example shown in FIG. 16B, a droplet 250 is present at the corresponding droplet operations electrode 216. Here, the presence of heating electrodes 446 ensures that droplet 250 is subjected to substantially uniform heat. Accordingly, the presence of heating electrodes 446 ensures that substantially no thermal gradients are present within droplet 250. The degree of uniform heat may be modulated by the size, shape, and/or height of heating electrodes 446.

A benefit of the electrode arrangement of thermal zone 444 shown in FIG. 16A and FIG. 16B is that heating may be provided both below and on multiple sides of the droplet 250, rather than heating from below the droplet only. That is, heating may be provided below droplet 250 using the droplet operations electrode 216. At the same time, heating may be provided on multiple sides of the droplet 250 using the heating electrodes 446. Further, because heating electrodes 446 are used for heating only and not for droplet operations, heating electrodes 446 may be formed of materials that are good thermal conductors but need not be good electrical conductors. For example, heating electrodes 446 may be formed of carbon, PEDOT, and the like.

Referring now to FIG. 17A and FIG. 17B is side views of a portion of microfluidics cartridge 110 and an example of a providing thermal control for supporting rapid PCR protocols. In one example, FIG. 17A shows a heater 448 mounted directly atop top substrate 212 of microfluidics cartridge 110. Heater 448 may be, for example, a large block heater for maintaining a stable and known boundary condition at the top of microfluidics cartridge 110.

Here, "boundary" means the air and cartridge boundary where heat can be lost. In one example, heater 448 may be used to ensure a stable and reliable boundary temperature of about 70° C., which is the extension temperature of a PCR protocol. The presence of heater 448 may eliminate the need for thermal feedback in microfluidics cartridge 110, simplifying the design and saving cost. Heater 448 may be provided on top substrate 212 only, on bottom substrate 210 only, or on both bottom substrate 210 and top substrate 212.

In another example, FIG. 17B shows that top substrate 212 may be replaced with a heated top substrate 450. In this example, heated top substrate 450 may include a PEDOT layer 452 by which the heating elements may be formed. In one example, PEDOT layer 452 may be provided such that substantially the entire top substrate 450 may be heated. In another example, PEDOT layer 452 may be patterned atop top substrate 450 such that heat may be provided at targeted locations only of microfluidics cartridge 110. PEDOT layer 452 may be provided on top substrate 212 only, on bottom substrate 210 only, or on both bottom substrate 210 and top substrate 212.

Referring now to FIG. 18 is a cross-sectional view of a portion of microfluidics structure 200 and an example of a heating/sensing element 462 for supporting rapid PCR protocols. In one example, heating/sensing element 462 may be a copper heating/sensing element 462. Further, heating/sensing element 462 may be installed in bottom substrate 210 such that it may protrude into droplet operations gap 214 and into a droplet (e.g., droplet 250). For example, heating/sensing element 462 may be installed in a via hole 464 in a PCB-based bottom substrate 210. In PCB technology, a via hole is a plated through-hole. The diameter of the via hole 464 in bottom substrate 210 may be tailored to receive a certain sized heating/sensing element 462. Heating/sensing element 462 may be sized to extend partially into droplet 250 or through the full volume (i.e., height) of droplet 250.

In, for example, a PCR protocol, the presence of heating/sensing element 462 may allow for rapid heating of, for example, droplet 250. Further, the presence of heating/sensing element 462 may allow for highly accurate sensing of the droplet temperature.

Referring now to FIG. 19 is a plan view of a portion of microfluidics structure 200 and an example of a thermal zone 466 for supporting rapid PCR protocols. Thermal zone 466 may be formed by a certain electrode configuration. Thermal zone 466 may include a line of droplet operations electrodes 216 set at different/alternating temperatures.

For example, in PCR protocols, standard droplet shuttling means shuttling a droplet back and forth between the same two electrodes. The droplet shuttling operation can cause bubbles to form within the droplet, which is undesirable. Therefore, to mitigate and/or reduce bubble formation, thermal zone 466 may include a line of any arrangement of electrodes 216DT (i.e., the denaturation zone), electrodes 216AT (i.e., the annealing zone), and/or electrodes 216ET (i.e., the extension zone). Electrode 216ET is an example of an ET electrode. In the example shown in FIG. 19, thermal zone 466 may include a line of alternating electrodes 216DT and electrodes 216AT. Accordingly, a droplet may be alternating between about 60° C. and about 95° C. as it moves down the line. Here, because the droplet is moving in one direction only, bubbles may be less likely to form. For example, in the one direction movement the bubbles may be left behind the droplet instead of being trapped within the droplet. Further, this one direction movement through the different temperatures may also benefit the mixing process.

Further, a benefit of the electrode arrangement of thermal zone 466 is that electrodes 216AT and 216DT may be positioned close together. Therefore, a droplet may be moved quickly (via droplet operations) from one electrode to the next for supporting rapid PCR protocols.

Referring now again to FIG. 1 through FIG. 19, in some embodiments, electrodes of microfluidics cartridge 110 may be dedicated or fixed at certain temperatures, such as at the annealing temperature, or at the extension temperature, or at the denaturation temperature. However, in other embodiments, the temperature of electrodes of microfluidics cartridge 110 may be set in programmable fashion and switched dynamically. For example, controller 112 and/or thermal control electronics 116 may provide dynamic control of certain electrodes. For example, one certain electrode may be set at the annealing temperature at one point in time. Then, the same electrode may be set at the extension temperature at another point in time. Then, the same electrode may be set at the denaturation temperature at yet another point in time.

Referring now to FIG. 20A and FIG. 20B is cross-sectional views of a portion of microfluidics structure 200 and examples of a sensing element 468 for supporting rapid PCR protocols. For example, sensing element 468 may be a copper sensing element. Sensing element 468 may be an example of thermal sensors 134 shown in FIG. 1. In one example, FIG. 20A shows sensing element 468 may be embedded in a droplet operations electrode 216. For example, sensing element 468 may be formed on the same PCB layer of bottom substrate 210 as the droplet operations electrode 216. In this example, because sensing element 468 may be formed on the same layer as the droplet operations electrode 216, sensing element 468 can detect the droplet temperature with little thermal delay. Further, this allows the droplet temperature to be very precisely measured.

In another example, FIG. 20B shows a sensing element 468 provided near the droplet operations electrode 216. For example, sensing element 468 may be formed beside or near droplet operations electrode 216 and on the same PCB layer of bottom substrate 210 as the droplet operations electrode 216. In this example, sensing element 468 may be close enough to the droplet operations electrode 216 to be touching the droplet (not shown).

In yet another example (not shown), droplet operations electrode 216 may be formed, for example, on a PCB layer 1 of bottom substrate 210. Then, sensing element 468 may be formed, for example, on a PCB layer 2 of bottom substrate 210 and directly below the droplet operations electrode 216. Then, a heating element (not shown) may be formed, for example, on a PCB layer 3 of bottom substrate 210 and directly below sensing element 468. In still another example (not shown), sensing element 468 may be formed by PEDOT printed on a solid droplet operations electrode 216.

Referring now to FIG. 21 is a plan view of a portion of microfluidics structure 200 and an example of laser heating for supporting rapid PCR protocols. In this example, a laser 470 may be provided with respect to microfluidics structure 200. In one example, laser 470 may be used to emit gold nanoparticles at droplet 250. Upon impinging on droplet 250 this light energy is converted to heat energy and thereby providing an efficient way of heating a droplet in, for example, a PCR protocol.

With the presence of laser 470, the system temperature may be regulated using, for example, infrared (IR) sensing, thermal sensors embedded in droplets, thermal sensors embedded in microfluidics cartridge 110, and the like.

Referring now again to FIG. 1 through FIG. 21, in any of the abovementioned configurations, certain features and/or variations may apply, for example, as follows:

(1) thermal sensing may be implemented on the dielectric layer 222 of the microfluidics cartridge 110 and in close proximity to the droplet. In one example, copper may be patterned on Kapton, which is a polyimide film used in flexible printed circuits (flexible electronics). This copper layer may also serve as a coplanar reference electrode;

(2) whereas droplet operations electrodes are typically formed of highly electrically and thermally conductive materials (e.g., copper, gold, or aluminum), instead droplet operations electrodes may be formed of less thermally conductive materials but still electrically conductive materials, such as carbon or other heater materials; and (3) whereas droplet operations electrodes are typically formed of highly electrically and thermally conductive materials (e.g., copper, gold, or aluminum), instead droplet operations electrodes may be formed of resistance materials, such as OhmegaPly® available from Quantic Omega (Culver City, CA). OhmegaPly® is a nickel phosphorous (NiP) metal alloy that is electrodeposited on to copper foil.

Modification of PCR Process Steps and/or Reaction Components for Rapid Thermocycling The disclosure provides methods for optimizing a thermocycling PCR amplification protocol performed on a microfluidics cartridge (or device). A PCR amplification protocol typically includes three temperature-sensitive process steps: denaturation, annealing, and extension. For example, a DNA template, e.g., double-stranded DNA is denatured at a denaturation temperature (e.g., about 95° C.) to generate single-stranded molecules. Amplification primers are then annealed at an annealing temperature (e.g., about 60° C.) to the complementary regions of the single-stranded molecules. The annealed primers are then extended at an extension temperature (e.g., about 70° C.) using a DNA polymerase. The denaturation, annealing, and extension process over the series of temperatures and time is referred to as one cycle of amplification. Multiple amplification cycles (e.g., 20 to 40 cycles) are typically used to produce a detectable product for analysis.

In one example, a thermocycling amplification protocol performed on a microfluidics cartridge (or device) may include, but is not limited to, the steps of:

(1) providing a microfluidics cartridge that includes an arrangement of droplet operations electrodes configured to provide a thermal zone comprising:
 a. a denaturation temperature zone;
 b. an annealing temperature zone;
 c. an extension temperature zone; and
 d. amplification reagents (e.g., primers, dNTPs, buffers, and enzymes);
  wherein the microfluidics device and reagents are configured for amplifying a target nucleic acid in a sample;
(2) providing a nucleic acid sample (e.g., a DNA sample);
(3) dispensing a sample droplet and transporting the sample droplet to the thermal zone;
(4) initiating the amplification protocol wherein initiating the amplification protocol may include:
 a. in the denaturation temperature zone, denaturing the DNA sample in the denaturation temperature zone to produce single-stranded molecules;
 b. performing a first annealing reaction in the annealing temperature zone to target a nucleic acid of interest; and
 c. performing a first extension reaction in the extension reaction zone to generate an amplification droplet potentially comprising a copy of the targeted nucleic acid;
(5) cycling the amplification droplet in the thermal zone two or more times to yield a detection droplet potentially comprising a plurality of target-specific amplicons; and
(6) transporting the detection droplet to a detection zone for determining, for example, the presence or absence of the targeted nucleic acid.

In some embodiments, the nucleic acid sample comprises RNA. In this case, a reverse transcription-PCR reaction (RT-PCR) protocol may be used to reverse transcribe the RNA into complementary DNA (cDNA) for input into the thermocycling reaction for amplification. cDNA may, for example, be prepared on the microfluidic device using an RT-PCR protocol.

In various embodiments, the disclosure provides methods for optimizing a thermocycling PCR amplification protocol performed on a microfluidics device.

Referring now to FIG. 22 is a flow diagram of an example of a method 2200 of optimizing a thermocycling PCR amplification protocol performed on a microfluidics device. Method 2200 may include, but is not limited to, the following steps.

At a step 2210, a microfluidics device configured for performing a thermocycling PCR amplification protocol is provided. For example, microfluidics cartridge 110 of microfluidics system 100 is provided. Microfluidics cartridge 110 may include one or more thermal zones (e.g., thermal zone 130) that includes thermally controlled droplet operations electrodes to provide a denaturation temperature (e.g., a DT electrode), an annealing temperature (e.g., an AT electrode), and an extension temperature (e.g., an ET electrode). In some embodiments, the annealing temperature and the extension temperature may be performed at the same temperature. In this case, the annealing and extension reactions may be performed at a single electrode (e.g., an AT/ET electrode). Microfluidics cartridge 110 may be pre-loaded with reaction components such as reverse transcription and amplification reagents (e.g., primers, dNTPs, buffers, and enzymes) and/or detection reagents.

At a step 2215, a nucleic acid sample potentially comprising a target nucleic acid is provided and a sample droplet is dispensed for processing. In some embodiments, the nucleic acid sample comprises DNA.

In some embodiments, the nucleic acid sample comprises RNA. In this case, a sample droplet comprising RNA is dispensed and a reverse transcription reaction is performed to reverse transcribed RNA into cDNA for subsequent PCR amplification. Accordingly, microfluidics cartridge 110 may further include a reverse transcription reaction zone and reagents for performing the reverse transcription reaction.

At a step 2220, the thermocycling PCR amplification protocol is initiated to yield an amplification droplet potentially comprising a copy of the targeted nucleic acid. For example, an initial PCR cycle may include: (i) transporting the sample droplet using droplet operations to a DT electrode and incubating the droplet at the denaturation temperature to yield a denatured sample droplet; (ii) transporting the denatured sample droplet using droplet operations to an AT electrode and performing a first annealing reaction to target a nucleic acid of interest to yield an annealed sample droplet; and (iii) transporting the annealed sample droplet to an ET electrode and incubating the annealed sample droplet at the extension temperature to yield an amplification droplet potentially comprising a copy of the targeted nucleic acid.

At a step 2225, the amplification droplet is cycled two or more times to yield a detection droplet potentially comprising a plurality of target-specific amplicons. For example, the amplification droplet may be cycled using droplet operations two or more times through thermal reactions zones 130 to yield a detection droplet potentially comprising a plurality of target-specific amplicons.

At a step 2230, a detection process is performed to determine the presence or absence of the targeted nucleic acid. For example, the detection droplet may be transported using droplet operations to a detection spot corresponding to the one or more thermal zones 130.

In various embodiments, one or more process steps and/or reaction components in method 2200 may be modified to improve the run time of a thermocycling PCR amplification assay performed using a microfluidics device.

In some embodiments, the microfluidic device (e.g., microfluidics cartridge 110) is configured for performing an RT-PCR protocol to reverse transcribe RNA into cDNA for input into the PCR amplification reaction. In a typical RT-PCR protocol, two different concentrations of magnesium (e.g., MgCl2) are typically used for the reverse transcription reaction and PCR amplification. The reverse transcription reaction typically uses a relatively high concentration of magnesium (e.g., up to about 11 mM MgCl2), which is a concentration that may be inhibitory for the subsequent PCR amplification reaction that typically is performed using a relatively lower concentration of magnesium (e.g., about less than 7 mM MgCl2). Consequently, an inappropriate magnesium concentration in either the RT reaction or the PCR amplification reaction may lead to reduced efficiency in one or both reactions, which may contribute to a longer overall protocol runtime.

The disclosure provides a method for increasing the efficiency of the reverse transcription reaction, while maintaining the integrity of the amplification reaction in an RT-PCR protocol performed on a microfluidics device.

In one embodiment, a chelating agent may be used to decrease the relatively high concentration of magnesium used in the reverse transcription reaction (step 2215), thereby providing a relatively lower concentration of magnesium for the subsequent amplification reaction (step 2220).

In one example, the method may include, but is not limited to, the steps of:
(1) providing a microfluidics device (e.g., microfluidics cartridge 110) that includes:
  a. a reverse transcription reaction zone (RT zone);
  b. thermal zones; and
  c. reagents for performing the reverse transcription reaction for converting RNA to cDNA, and subsequent PCR amplification of cDNA;
    wherein a chelating agent is provided to decrease the concentration of magnesium used in the reverse transcription reaction to a level suitable for the subsequent PCR amplification;
(2) performing the reverse transcription reaction to produce a cDNA template droplet;
(3) combining the cDNA template droplet with a chelating reagent to yield a cDNA amplification droplet;
    wherein the concentration of the chelating agent in the cDNA amplification droplet is sufficient to provide a concentration of magnesium suitable for PCR amplification; and
(4) performing the PCR amplification reaction to yield a detection product.

In one embodiment, the chelating agent may be provided as a dried reagent spot on a certain droplet operations electrode (e.g., a DT electrode). For example, a chelating agent may be provided on a certain droplet operations electrode and a cDNA template droplet may be transported to the droplet operations electrode and used to reconstitute the dried chelating agent, thereby yielding a cDNA amplification droplet comprising a concentration of magnesium suitable for PCR amplification.

In one embodiment, the chelating agent may be provided in a reagent solution that may be dispensed and combined with the cDNA template droplet to yield a cDNA amplification droplet comprising a concentration of magnesium suitable for PCR amplification.

In one embodiment, the chelating agent is EDTA. For example, an EDTA reagent may be provided at a concentration of about 4 mM, which is a concentration that may be used to decrease the magnesium concentration in the cDNA template droplet (e.g., from about 11 mM) to a concentration in the amplification droplet suitable for PCR amplification (e.g., about 7 mM or less).

In a rapidly cycled PCR protocol, reaction components such as enzymes, primers, and dNTPs may become limiting. For example, in a rapidly cycled PCR protocol, enzymes used (e.g., reverse transcriptase and/or DNA polymerase) may be exposed to very fast and high temperature changes. This repeated exposure to high temperature can cause the enzymes to denature and/or stick to device surfaces. Denaturation and/or sticking of the enzymes can negatively impact the efficiency of an amplification reaction.

The disclosure provides a method for maintaining the integrity of enzymes used in one or more process steps of a PCR protocol performed on a microfluidics device. The method of the invention may, for example, be used for PCR amplification protocols that use DNA and/or RNA as a sample input.

In various embodiments, the processing enzymes (e.g., reverse transcriptase and/or DNA polymerase) may be anchored on a solid surface. The solid surface may be a bead. The solid surface may be a certain electrode in a thermal zone on the microfluidic device. The solid surface may be a surface of the top plate of the microfluidic device.

In one embodiment, processing enzymes used in a PCR protocol may be anchored in one or more thermal zones on the microfluidic device. For example, processing enzymes may be anchored in a lower temperature zone, e.g., a reverse transcription zone, and/or at a thermally controlled electrode in a thermal zone (e.g., an AT electrode, an ET electrode, or a combined AT/ET electrode in thermal zone 130). Anchoring the processing enzymes to a solid surface may be used to reduce the loss of enzyme activity during repeated cycling (e.g., 45 cycles) of a reaction droplet between the different temperature zones used in a PCR protocol.

Referring now to FIG. 23 is a schematic diagram of an example of a process 2300 for maintaining the integrity of enzymes used in a PCR protocol performed on a microfluidics device. In this example, as shown in panel A, an array of droplet operations electrodes 2310 may include a DT electrode 2315 and a combined annealing/extension electrode 2320 (i.e., an AT/ET electrode 2320). AT/ET electrode 2320 may include a plurality of beads 2322 with DNA polymerase anchored thereon. Referring now to panel B, in a PCR amplification reaction, an amplification droplet 2330 may be transported to DT electrode 2315 for denaturation of double-stranded DNA to single-stranded molecules initiate a first amplification cycle. Referring now to panel C, at the end of the denaturation step, amplification droplet 2330 may be transported to AT/ET electrode 2320 for annealing of target-specific amplification primers and extension of the primers by DNA polymerase bound to beads 2322 to complete the first amplification cycle. Referring now to panel D, at the completion of the first amplification cycle, amplification droplet 2330 may be transported away from beads 2322 (with DNA polymerase anchored thereon) on AT/ET electrode 2320 and back to DT electrode 2315 to initiate another amplification cycle.

In one embodiment, anchoring reverse transcriptase and DNA polymerase in a thermal zone may facilitate an RT-PCR protocol wherein the reverse transcription reaction may be performed simultaneously with the amplification reaction. For example, performing the reverse transcription reaction concurrent with the amplification reaction may be used to further increase the output product for detection.

The disclosure provides a method for augmenting (i.e., resupplying) reaction components (e.g., primers and/or dNTPs) that may be depleted in one or more process steps of a PCR protocol performed on a microfluidics device. The method of the invention may, for example, be used for PCR protocols that use DNA or RNA as a sample input.

In one embodiment, the reaction components may be supplied on a bead surface in a reagent droplet and delivered (using droplet operations) to a thermal zone at an appropriate time in an PCR protocol. In another example, the reaction components may be supplied in a hydrogel bead in a reagent droplet and delivered (using droplet operations) to a thermal zone at an appropriate time in a PCR protocol.

In some embodiments, reaction components may be supplied as a dried reagent spot at a certain droplet operations electrode and reconstituted (using droplet operations) at an appropriate time in an PCR protocol. For example, a buffer droplet may be transported to a dried reagent spot using droplet operations to reconstitute the dried reagent to yield a reconstituted reagent droplet. The reconstituted reagent droplet may then be delivered (using droplet operations) to a thermal zone at an appropriate time in an PCR protocol. In another example, a PCR reaction droplet may be transported to a dried reagent spot using droplet operations to yield a re-supplied PCR reaction droplet.

In one embodiment, reaction components may be provided in a dried reagent patch at a certain droplet operations electrode in a thermal zone (e.g., an AT electrode, an ET electrode, and/or a combined AT/ET electrode in thermal zone 130).

In another embodiment, reaction components may be provided in a dried reagent patch at a certain droplet operations electrode (e.g., a certain droplet operations electrode 216) that is outside of a thermal zone (e.g., thermal zone 130).

The disclosure provides methods for maintaining the integrity of primers used in a PCR protocol performed on a microfluidic device. In various embodiments, the primer (e.g., reverse primers and/or amplification primers) may be immobilized on a solid surface. The solid surface may be a bead. The solid surface may be a certain electrode in a thermal zone on the microfluidic device. The solid surface may be a surface of the top plate of the microfluidic device.

In some embodiments, reverse transcription primers may be immobilized on a bead surface. Immobilizing the reverse transcription primers on a solid surface such as a bead may be used to facilitate transitioning from a reverse transcription reaction zone to an amplification thermal zone.

In some embodiments, forward and/or reverse amplification primers may be immobilized on a solid surface. In one embodiment, both the forward and reverse amplification primers may be immobilized on a solid surface. In another embodiment, the forward primer may be immobilized on a solid surface and the reverse primer may be provided in a solution. In yet another embodiment, the reverse primer may be immobilized on a solid surface and the forward primer may be provided in a solution. Immobilization of forward and/or reverse amplification primers on a solid surface may, for example, be used to reduce the formation of primer-dimers during the amplification process. In another example, immobilizing the forward and/or reverse primers on a solid surface such as a bead may be used to facilitate "lawn-mediated" amplification wherein bead-bound amplicons in a reaction droplet may be readily transported to different thermal zones during the amplification process.

The disclosure provides a method for priming a target-specific amplification reaction for rapid cycling on a microfluidics device. The method of the invention uses forward and reverse amplification primers that include a target-specific sequence and a generic "fast amplifying" sequence. Referring now to FIG. 24 is a schematic diagram of an example of a fast-cycling amplification primer pair. A primer pair for amplifying a target nucleic acid 2410 may include a forward primer 2420*a* and a reverse primer 2420*b*. Forward primer 2420*a* and reverse primer 2420*b* each may include a 3' target-specific sequence (designated as "nnnn") and a 5' generic fast amplifying sequence (designated as "NNN"). The sequence of the generic sequence is selected to facilitate rapid PCR amplification on a microfluidics device without reducing target-specificity in the amplification reaction.

In some embodiments, the shape of a reaction droplet may be used to provide for more rapid and uniform heating of a reaction droplet during a PCR amplification protocol, thereby improving the efficiency of the protocol.

Referring now to FIG. 25A and FIG. 25B is a schematic diagram of an example of an elongated droplet and a donut shaped droplet, respectively, that may be used to provide for more rapid and uniform heating of a reaction droplet during thermocycling on a microfluidics device. For example, FIG. 25A shows an elongated droplet 2520 that spans three droplet operations electrodes 2510. FIG. 25B shows examples of donut shaped droplets 2520 atop respective droplet operations electrodes 2510. Elongated droplet 2520 and donut shaped droplets 2520 may be examples of droplet shapes that are optimized for rapid heating.

In some embodiments, the microfluidic device (e.g., microfluidics cartridge 110) may be configured to provide an assay readout in real time. For example, in a real-time PCR amplification reaction, data is collected as the reaction is proceeding and may not rely on post PCR detection methods (i.e., as in endpoint PCR detection). Because amplification data is collected in real time, fewer amplification cycles may be used thereby reducing the overall protocol runtime.

The invention provides a method for detecting amplification of a target nucleic acid in real time on a microfluidics device. In various embodiments, the method uses an enzyme-linked PCR amplification reaction for detection of a target nucleic acid. In one embodiment, an enzyme-linked PCR amplification reaction may include: (i) a target-specific probe comprising a releasable enzyme inhibitor; (ii) an enzyme subject to inhibition by the inhibitor; and (iii) a substrate wherein in the presence of active enzyme a fluorescent product is produced. Examples of enzymes that may be used include, but are not limited to, fluorescence producing enzymes such as luciferase, beta-galactosidase, and pH changing enzymes. In some embodiments, the enzyme is a fluorophore. Examples of enzyme inhibitors that may be used include, but are not limited to, small molecules, metal cofactor chelators, and proteins. In some embodiments, the enzyme inhibitor is a quencher. Examples of substrates that may be used include single fluorophores, bi-chromophore, and multi-fluorophore systems. In some embodiments, a single fluorophore includes, for example, a 5' triphosphate form of a fluorescent natural base analog or a fluorescent natural base analog incorporated into a probe or a template strand. In some embodiments, a bi-chromophore system includes, for example, molecular beacons or TaqMan probes. In some embodiments, the molecular beacons may include a step-loop structure wherein the loop contains partial sequence complementarity to the target sequence. In some embodiments, the molecular beacons may include a step-loop structure wherein the stem contains short complementary sequences to bring the 3' and 5' ends of the molecular probe into close proximity. In some embodiments, the fluorescent signal is mediated by a fluorescence resonance energy transfer (FRET) mechanism. In some embodiments, the substrate is luciferin. In some embodiments, the substrate is lactose, galactose, or 5-bromo-4-chloro-3-indoyl-β-D-galactopyranoside (also known as X-gal). Referring now to FIG. 26A is a schematic diagram of an example of an enzyme linked PCR process 2600 for real time detection of amplification products on a microfluidics device. For example, a target-specific probe 2610 comprising a releasable enzyme inhibitor 2620 is combined in an amplification reaction droplet (not shown) with an enzyme 2625 and a substrate (not shown). If a target nucleic acid is present in the reaction droplet, probe 2610 will bind to the target sequence. In some embodiments, probe 2610 is a single stranded nucleic acid. During amplification, DNA polymerase will cleave probe 2610 bound to the target sequence and release enzyme inhibitor 2620. In some embodiments, the single stranded nucleic acid probe 2610 induces cleavage by DNA polymerase when hybridized to a target nucleic acid. The released enzyme inhibitor 2620 is now available to bind enzyme 2625, thereby inhibiting the activity of the enzyme. Because the activity of the enzyme is inhibited, the substrate is not converted to a fluorescent product.

Referring now to FIG. 26B is a schematic diagram of a pair of plots 2640 and 2645 showing representative negative and positive amplification results, respectively, for an enzyme-linked PCR process. Referring to plot 2640, in the absence of the target nucleic acid, the probe 2610 is unbound and therefor uncleaved by DNA polymerase during the amplification reaction. Because probe 2610 is uncleaved, enzyme inhibitor 2620 is bound, and enzyme 2625 is active to cleave the substrate thereby producing a steady linear increase in fluorescence.

Referring to plot 2645, in the presence of the target nucleic acid, probe 2610 binds to the target site. During the amplification reaction, the bound probe 2610 is cleaved by DNA polymerase, thereby releasing enzyme inhibitor 2620, which then binds to enzyme 2625 effectively inactivating the enzyme. As the amplification reaction progresses, the amount of released enzyme inhibitor 2620 is increased to a level that is sufficient to effectively inhibit the activity of enzyme 2625 on the substrate, thereby stopping the linear increase in fluorescence.

In one embodiment, an enzyme-linked PCR amplification reaction may include: (i) a target-specific probe comprising an enzyme inhibitor and an enzyme subject to inhibition by the inhibitor; and (ii) a substrate wherein in the presence of active enzyme a detectable product is produced. Examples of enzymes that may be used include, but are not limited to, fluorescence producing enzymes and pH changing enzymes. Examples of enzyme inhibitors that may be used include, but are not limited to, small molecules, metal cofactor chelators, and proteins.

Referring now to FIG. 27A is a schematic diagram of an example of an enzyme-linked PCR process 2700 that uses a target-specific probe that includes an enzyme and enzyme inhibitor for real time detection of amplification products. In this example, an enzyme 2710 and an enzyme inhibitor 2715 are anchored on a target-specific probe 2720. Enzyme 2710 and enzyme inhibitor 2715 are anchored on probe 2720 in proximity such that the activity of enzyme 2710 is inhibited by enzyme inhibitor 2715. Probe 2720 (with enzyme 2710/enzyme inhibitor 2715 complex thereon) is combined in an amplification reaction droplet (not shown) with a substrate (not shown). In some embodiments, probe 2720 is a single stranded nucleic acid. If a target nucleic acid is present in the reaction droplet, probe 2720 will bind to the target site. During amplification, DNA polymerase will cleave probe 2720, thereby separating the enzyme/inhibitor complex. In some embodiments, the single stranded nucleic acid probe 2720 induces cleavage by DNA polymerase when hybridized to a target nucleic acid. Enzyme 2710 is now available to bind the substrate and generate a detection signal (e.g., a fluorescence signal). In some embodiments, 2710 is a fluorophore and 2715 is a quencher. In some embodiments, 2715 is a fluorophore and 2710 is a quencher.

In one embodiment, an enzyme-linked PCR amplification reaction may include: (i) a target-specific probe comprising a first enzyme half anchored to one strand and a second enzyme half anchored to the other strand in a configuration to yield an inactive enzyme; and (ii) a substrate wherein in the presence of an active enzyme a detectable product is produced. Examples of enzymes that may be used include, but are not limited to, fluorescence producing enzymes and pH changing enzymes.

Referring now to FIG. 27B is a schematic diagram of an example of an enzyme-linked PCR process 2730 using a target specific probe that includes an inactive split enzyme for real time detection of amplification products. In this example, a first enzyme half 2740a and a second enzyme half 2740b are anchored on a target-specific probe 2720. Enzyme half 2740a and enzyme half 2740b are anchored on probe 2720 in a configuration such that the enzyme is inactive. Probe 2720 (with enzyme half 2740a and enzyme half 2740b thereon) is combined in an amplification reaction droplet (not shown) with a substrate (not shown). If a target nucleic acid is present in the reaction droplet, probe 2720 will bind to the target site. During amplification, DNA polymerase will cleave probe 2720, thereby releasing enzyme half 2740a and enzyme half 2740b. Enzyme half 2740a and enzyme half 2740b interact to form an active enzyme which can bind the substrate and generate a detection signal (e.g., a fluorescence signal). In some embodiments, 2740a and 2740b are fluorophores that produce a signal when combined through, for example, a fluorescence resonance energy transfer (FRET) mechanism.

In one embodiment of a probe-based detection approach, a double probe approach may be used to target a relatively longer amplicon, thereby increasing the detection signal.

The disclosure provides a method for reducing cycle number and increasing the detection signal in an endpoint PCR amplification reaction performed on a microfluidics device. In one embodiment, multiple target-specific amplification reactions are performed simultaneously in thermal reactions zones on the microfluidic device and then transported to a detection spot on the device for endpoint analysis.

In one example, the method may include, but is not limited to, the steps of:

(1) providing a microfluidics device (e.g., microfluidics cartridge 110) that includes:
   a. multiple thermal zones configured for amplifying a target nucleic acid in multiple sample droplets;
   b. reagents for performing multiple simultaneous amplification reactions; and
   c. a detection spot wherein the detection spot includes a plurality of capture molecules for capturing target-specific amplicons;
(2) providing a nucleic acid sample potentially comprising a target nucleic acid;
(3) dispensing multiple sample droplets and transporting the sample droplets to individual thermal zones;
(4) cycling the sample droplets in the thermal zones two or more times (e.g., 5 to 10 cycles) to yield multiple detection droplets potentially comprising a plurality of target-specific amplicons;
(5) transporting each detection droplet to the detection spot comprising the target-specific capture molecules wherein the target-specific amplicons, if present, are captured; and
(6) performing the detection process to determine the presence of absence of the target-nucleic acid.

During a thermocycling reaction one or more components in the reaction may become limiting. The disclosure provides a method for re-supplying one or more reaction components (e.g., DNA polymerase, primers, and/or dNTPs) during a PCR amplification protocol performed on a microfluidics device.

In one embodiment, one or more reaction components (e.g., DNA polymerase, primers, and/or dNTPs) may be delivered to a thermal zone during thermocycling. For example, a reagent droplet comprising one or more reaction components may be combined with a reaction droplet at a certain time in the amplification cycle.

The specificity and efficiency of a PCR amplification protocol performed on a microfluidics device may be increased by enriching a sample for one or more targets of interest prior to input into the amplification protocol.

In one embodiment, a sample may be pre-enriched for viral RNA for input into an RT-PCR reaction. In one example, a size specific capture/precipitation process may be used to enrich for viral RNA. In another example, a PEG-based method may be used to enrich for viral RNA. In one example, a capture surface (e.g., the surface of a capture bead) may be coated with a viral RNA-specific capture molecule. The capture bead may be used in a sample preparation protocol to selectively enrich for the target viral nucleic acid to yield an enriched sample droplet. The enriched sample droplet may be used as input for an RT-PCR amplification protocol.

Rapid cycling in a PCR amplification protocol performed on a microfluidics device may be facilitated by decreasing the temperature differential between the denaturation and annealing steps in the amplification process (i.e., reducing the "ramp" time needed to transition between the denaturation and annealing reactions). Additionally, a relatively higher temperature for the annealing step may facilitate using the same thermal zone for performing both the annealing and extension steps in a PCR amplification protocol performed on a microfluidic device.

In one embodiment, a lower temperature differential between the denaturation and annealing steps in the amplification process may be achieved by using primers that may be annealed and extended at relatively higher annealing/extension temperature (e.g., of about 70°), thereby reducing the temperature differential between the denaturation step (e.g., performed at about 95° C.) and the annealing/extension reaction.

In one embodiment, a relatively high melting temperature for a primer/amplicon pair may be achieved through selection of appropriate primer sequences. In another example, a relatively high melting temperature for a primer/amplicon pair may be achieved by using primers comprising "locked nucleic acid" (LNA) residues. In yet another example, a relatively high melting temperature for a primer/amplicon pair may be achieved through the use minor groove-binding characteristics of the primer.

In some cases, the top and/or bottom substrate of a droplet actuator includes a PCB substrate that is coated with a dielectric, such as a polyimide dielectric, which may in some cases also be coated or otherwise treated to make the droplet operations surface hydrophobic. Various materials are also suitable for use as the dielectric component of the droplet actuator. In some cases, the top and/or bottom substrate of a droplet actuator includes a glass or silicon substrate on which features have been patterned using process technology borrowed from semiconductor device fabrication including the deposition and etching of thin layers of materials using microlithography. The top and/or bottom substrate may consist of a semiconductor backplane (i.e., a thin-film transistor (TFT) active-matrix controller) on which droplet operations electrodes have been formed.

Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution.

Terms and Definitions

The term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

The terms "comprise," "comprises," "comprising," "include," "includes," and "including," are intended to be non-limiting, such that recitation of items in a list is not to the exclusion of other like items that may be substituted or added to the listed items.

Terms like "preferably," "commonly," and "typically" are used herein without limiting the scope of the claimed embodiments or to imply that certain features are critical or essential to the structure or function of the claimed embodiments. These terms are intended to highlight alternative or additional features that may or may not be utilized in a particular embodiment of the disclosure.

The terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

The term "substantially" is utilized herein to represent the inherent degree of uncertainty that may be attributed to any quantitative comparison, value, measurement, or other representation and to represent the degree by which a quantitative representation may vary from a stated reference without resulting in a change in the basic function of the subject matter at issue.

"Activate," with reference to one or more electrodes, means affecting a change in the electrical state of the one or more electrodes which, in the presence of a droplet, results in a droplet operation. Activation of an electrode can be accomplished using alternating current (AC) or direct current (DC). Any suitable voltage may be used. For example, an electrode may be activated using a voltage which is greater than about 5 V, or greater than about 20 V, or greater than about 40 V, or greater than about 100 V, or greater than about 200 V or greater than about 300 V. Further, electrode may be activated using a positive and/or negative voltage relative to system ground. Further, deactivated electrodes may be held at ground or floated. The suitable voltage being a function of the dielectric's properties such as thickness and dielectric constant, liquid properties such as viscosity and many other factors as well. Where an AC signal is used, any suitable frequency may be employed. For example, an electrode may be activated using an AC signal having a frequency from about 1 Hz to about 10 MHz, or from about 1 Hz and 10 KHz, or from about 10 Hz to about 240 Hz, or about 60 Hz.

"Droplet" means a volume of liquid on a droplet actuator. Typically, a droplet is at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components.

"Droplet Actuator" means a device for manipulating droplets. Microfluidics devices, microfluidics cartridges, digital microfluidics (DMF) devices, and DMF cartridges are examples of droplet actuators. Certain droplet actuators will include one or more substrates arranged with a droplet operations gap therebetween and electrodes associated with (e.g., patterned on, layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Droplet actuators will include various electrode arrangements on the bottom and/or top substrates. During droplet operations it is preferred that droplets remain in continuous contact or frequent contact with a ground or reference electrode. A ground or reference electrode may be associated with the top substrate facing the gap, the bottom substrate facing the gap, or within the gap itself. Where electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. Where multiple substrates are used, a spacer may be provided between the substrates to determine the height of the gap therebetween and define on-actuator dispensing reservoirs. The spacer height may, for example, be from about 5 μm to about 1000 μm, or about 100 μm to about 400 μm, or about 200 μm to about 350 μm, or about 250 μm to about 300 μm, or about 275 μm. The spacer may, for example, be formed of features or layers projecting from the top or bottom substrates, and/or a material inserted between the top and bottom substrates. One or more openings may be provided in the one or more substrates for forming a fluid path through which liquid may be delivered into the droplet operations gap.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. Impedance and/or capacitance sensing and/or imaging techniques may sometimes be used to determine or confirm the outcome of a droplet operation. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may be completed within about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to or larger than the electrowetting area; in other words, 1×-, 2×-3×-droplets are usefully controlled and/or operated using 1, 2, and 3 electrodes, respectively. If the droplet footprint is greater than number of electrodes available for conducting a droplet operation at a given time, the difference between the droplet size and the number of electrodes should typically not be greater than 1; in other words, a 2× droplet is usefully controlled using 1 electrode and a 3× droplet is usefully controlled using 2 electrodes. When droplets include beads, it is useful for droplet size to be equal to the number of electrodes controlling the droplet, e.g., transporting the droplet.

"Filler fluid" means a fluid associated with a droplet operations substrate of a droplet actuator, which fluid is sufficiently immiscible with a droplet phase to render the droplet phase subject to electrode-mediated droplet operations. For example, the droplet operations gap of a droplet actuator is typically filled with a filler fluid. The filler fluid may, for example, be or include a low-viscosity, low-surface tension oil, such as silicone oil or hexadecane. The filler fluid may be or include a halogenated oil, such as a fluorinated or perfluorinated oil. The filler fluid may fill the entire gap of the droplet actuator or may only coat one or more surfaces of the droplet actuator or may only surround a droplet (i.e., an "oil-shell") and the droplet brings its own oil with it. Filler fluids may be selected to improve droplet operations and/or reduce loss of reagent or target substances from droplets, reduce formation of unwanted microdroplets, reduce cross contamination between droplets, reduce contamination of droplet actuator surfaces, reduce degradation of droplet actuator materials, reduce evaporation of droplets, and so on. For example, filler fluids may be selected for compatibility with droplet actuator materials. As an example, fluorinated filler fluids may be usefully employed with fluorinated surface coatings. In another example, fluorinated filler fluids may be used to dissolve surface coatings (e.g., Fluorinert fc-40 may be a solvent for Teflon AF). Fluorinated filler fluids are useful to reduce loss of lipophilic compounds, such as umbelliferone substrates like 6-hexadecanoylamido-4-methylumbelliferone substrates (e.g., for use in Krabbe, Niemann-Pick, or other assays); Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc. Composition of the filler fluid, including surfactant doping, may be selected for performance with reagents or samples used in the specific assay protocols and effective interaction or non-interaction with droplet actuator materials. For example, fluorinated oils may in some cases be doped with fluorinated surfactants, e.g., Zonyl FSO-100 (Sigma-Aldrich) and/or others.

"Reservoir" means an enclosure or partial enclosure configured for holding, storing, or supplying liquid. A droplet actuator system of the disclosure may include on-cartridge reservoirs and/or off-cartridge reservoirs. On-cartridge reservoirs may be (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface; or (3) hybrid reservoirs which have on-actuator regions and off-actuator regions. An example of an off-actuator reservoir is a reservoir in the top substrate. An off-actuator reservoir is typically in fluid communication with an opening or flow path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. A system using an off-cartridge reservoir will typically include a fluid passage means whereby liquid may be transferred from the off-cartridge reservoir into an on-cartridge reservoir or into a droplet operations gap.

"Washing" with respect to washing a surface, such as a hydrophilic surface, means reducing the amount and/or concentration of one or more substances in contact with the surface or exposed to the surface from a droplet in contact with the surface. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent or buffer.

The terms "top," "bottom," "over," "under," and "on" are used throughout the description with reference to the relative positions of components of the droplet actuator, such as relative positions of top and bottom substrates of the droplet actuator. It will be appreciated that in many cases the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface. In one example, filler fluid can be considered as a dynamic film between such liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range.

Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the subject matter. For example, the term "about," when referring to a value can be meant to encompass variations of, in some embodiments ±100%, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Various modifications and variations of the disclosed methods, compositions and uses of the disclosure will be apparent to the skilled person without departing from the scope and spirit of the disclosure. Although the subject matter has been disclosed in connection with specific preferred aspects or embodiments, it should be understood that the subject matter as claimed should not be unduly limited to such specific aspects or embodiments.

The subject matter may be implemented using hardware, software, or a combination thereof and may be implemented in one or more computer systems or other processing systems. In one aspect, the subject matter is directed toward one or more computer systems capable of carrying out the functionality described herein.

Although the foregoing subject matter has been described in some detail by way of illustration and example for purposes of clarity of understanding, it will be understood by those skilled in the art that certain changes and modifications can be practiced within the scope of the appended claims.

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

What is claimed is:

1. A method of thermal cycling a droplet comprising:
   (a) providing a device comprising an array of electrodes wherein the array comprises first and second electrodes within a dielectric layer, and wherein:
      (i) the first and second electrodes are separated by a gap, the gap comprising a space between the electrodes, the space being about 50 µM to about 200 µM, and the gap being a portion of the dielectric layer; and
      (ii) the gap dielectric layer portion is configured to have a different thermal conductivity relative to the first and second electrodes;
   (b) establishing a first temperature at the first electrode and a second temperature at the second electrode, and a thermal zone between the first electrode and the second electrode, the thermal zone comprising a temperature gradient;
   (c) using one or more droplet operations mediated by the first and second electrodes to cycle a droplet between the first temperature and the second temperature.

2. The method of claim 1 wherein:
   (a) establishing the first thermal zone comprises establishing the first thermal zone at a nucleic acid annealing temperature; and
   (b) establishing the second thermal zone comprises establishing the second thermal zone at a nucleic acid denaturing temperature.

3. The method of claim 1 wherein:
   (a) the droplet comprises nucleic acid amplification reagents; and
   (b) using one or more droplet operations mediated by the first and second electrodes to transport the droplet between the first thermal zone and the second thermal zone results in nucleic acid amplification in the droplet.

4. The method of claim 1 further comprising:
   (a) filling the gap with a plurality of electrodes that are smaller than the first and second electrodes, wherein each electrode of the plurality of electrodes is thermally insulated from the others.

5. The method of claim 4, wherein a steep thermal gradient is maintained between the first and second thermal zones.

6. The method of claim 1, wherein each cycle is accomplished in a time of less than or equal to about 5,000 ms.

7. The method of claim 1, wherein each cycle is accomplished in a time of less than or equal to about 1,000 ms.

8. The method of claim 1, wherein each cycle is accomplished in a time of less than or equal to about 100 ms.

9. The method of claim 1, wherein the electrodes have a size ranging from about 50 µm to about 500 µm.

10. The method of claim 1, wherein the gap comprises an increased thermal mass relative to the unit sized droplet operations electrodes.

11. The method of claim 1, wherein a thermal conductivity in the gap is reduced.

12. The method of claim 1, wherein the gap comprises an array of linear electrodes that are smaller than the first and second electrodes.

13. The method of claim 1, wherein the distance between a center of the first electrode and a center of the second electrode is less than about 1 mm.

14. The method of claim 1, wherein the distance between a center of the first electrode and a center of the second electrode is less than about 500 µm.

15. The method of claim 1, wherein the droplet has a size that is sufficiently small that the droplet does not overlap an adjacent electrode when situated atop an activated electrode.

16. The method of claim 1, the device further comprising a substrate and wherein the gap comprises an indentation in the substrate or a top substrate that is configured to have reduced thermal conductivity relative to the unit sized electrodes.

17. The method of claim 16 further comprising using one or more droplet operations mediated by the first and second electrodes together with passive flow into the indentation to transport the droplet between the first thermal zone and the second thermal zone.

18. The method of claim 1, wherein there is nucleic acid amplification in the droplet.

* * * * *